United States Patent
Cho

(10) Patent No.: US 11,666,272 B2
(45) Date of Patent: Jun. 6, 2023

(54) PAIN-MONITORING DEVICE AND METHOD

(71) Applicant: IKOOB CO., LTD, Seoul (KR)

(72) Inventor: Jae-hyoung Cho, Seoul (KR)

(73) Assignee: IKOOB CO., LTD, Seoul (KR)

( * ) Notice: Subject to any disclaimer, the term of this patent is extended or adjusted under 35 U.S.C. 154(b) by 0 days.

(21) Appl. No.: 17/608,980

(22) PCT Filed: Aug. 7, 2019

(86) PCT No.: PCT/KR2019/009880
§ 371 (c)(1),
(2) Date: Nov. 4, 2021

(87) PCT Pub. No.: WO2020/230952
PCT Pub. Date: Nov. 19, 2020

(65) Prior Publication Data
US 2022/0202361 A1 Jun. 30, 2022

(30) Foreign Application Priority Data

May 13, 2019 (KR) .......................... 10-2019-0055519

(51) Int. Cl.
*A61B 5/00* (2006.01)
*A61B 5/22* (2006.01)

(52) U.S. Cl.
CPC ............ *A61B 5/4824* (2013.01); *A61B 5/225* (2013.01); *A61B 5/743* (2013.01); *A61B 5/748* (2013.01); *A61B 2562/0247* (2013.01)

(58) Field of Classification Search
CPC ....... A61B 5/4824; A61B 5/225; A61B 5/743; A61B 5/748; A61B 2562/0247;
(Continued)

(56) References Cited

U.S. PATENT DOCUMENTS 9,981,131 B2 * 5/2018 Kent .................... A61N 1/3614
2009/0005649 A1 1/2009 Baird et al.
(Continued)

FOREIGN PATENT DOCUMENTS

CA 2782114 A1 * 1/2013 ............ A61B 5/225
EP 2359747 A1 8/2011
(Continued)

OTHER PUBLICATIONS

International Search Report of PCT/KR2019/009880, dated Feb. 11, 2020, English translation.
(Continued)

*Primary Examiner* — Sean P Dougherty
(74) *Attorney, Agent, or Firm* — STIP Law Group, LLC

(57) ABSTRACT

A pain-monitoring device and method according to an embodiment of the present disclosure is a pain-monitoring device for obtaining information related to a pain of a user and providing a service of monitoring the pain of the user, includes: an input unit sensing pain-related input of the user; a display unit outputting pain-related information; and a control unit controlling the input unit and the display unit, in which the input unit includes: a touch input unit sensing touch input of the user; and a pressure measurement unit measuring pressure input of the user, and the control unit creates user-input pain information in accordance with the sensed pressure input and touch input.

5 Claims, 10 Drawing Sheets

[FIG. 2]

(58) Field of Classification Search
CPC ............ A61B 2560/0223; A61B 5/742; A61B 5/7475; A61B 5/0002
See application file for complete search history.

(56) References Cited

U.S. PATENT DOCUMENTS

| | | | | |
|---|---|---|---|---|
| 2011/0066078 A1* | 3/2011 | Sarvazyan | ............ | A61B 5/4821 600/587 |
| 2011/0082384 A1* | 4/2011 | Harte | .................. | A61B 5/4827 600/557 |
| 2013/0046205 A1* | 2/2013 | Schaffner | ............. | A61B 5/4824 600/587 |
| 2014/0235965 A1* | 8/2014 | Tran | ........................ | A61B 8/06 600/407 |
| 2016/0198996 A1* | 7/2016 | Dullen | ............... | A61B 5/02055 600/595 |
| 2016/0306946 A1* | 10/2016 | Harbut | ............... | A61N 1/37247 |
| 2017/0242965 A1* | 8/2017 | Simon | ................... | G16H 10/60 |
| 2019/0019573 A1* | 1/2019 | Lake | .................... | A61B 5/4842 |
| 2019/0239800 A1* | 8/2019 | Zeller | ............... | A61B 5/4824 |

FOREIGN PATENT DOCUMENTS

| | | | | |
|---|---|---|---|---|
| EP | 2543317 A1 * | 1/2013 | ............. | A61B 5/225 |
| EP | 3219257 B1 | 2/2019 | | |
| JP | 2019010414 A | 1/2019 | | |
| KR | 101263184 B1 | 5/2013 | | |
| KR | 20140094912 A | 7/2014 | | |
| KR | 20170020049 A | 2/2017 | | |
| KR | 20170089727 A | 8/2017 | | |
| WO | WO-2011079966 A1 * | 7/2011 | ........... | A61B 5/4824 |
| WO | WO-2011080237 A1 * | 7/2011 | ............. | A61B 5/441 |
| WO | WO-2014134631 A1 * | 9/2014 | ........... | A61B 5/0053 |
| WO | WO-2017088047 A1 * | 6/2017 | ........... | A61B 5/0488 |

OTHER PUBLICATIONS

Carepeutic Digital Talking Hand Grip Exerciser, amazon, https://www.amazon.com/Carepeutic-Digital-Talking-Hand-Exerciser/dp/B009QV5J6E?th=1, Nov. 2013.

The partial supplementary European search report of EP 19 92 8434, dated Feb. 1, 2023.

Steven E. Harte el at, Development and validation of a pressure-type automated quantitative sensory testing system fro point-of-care pain assessment, Med Biol Eng Comput, 2013, vol. 51, pp. 633-644, Spinger, Berlin, Germany.

* cited by examiner

[FIG. 1]
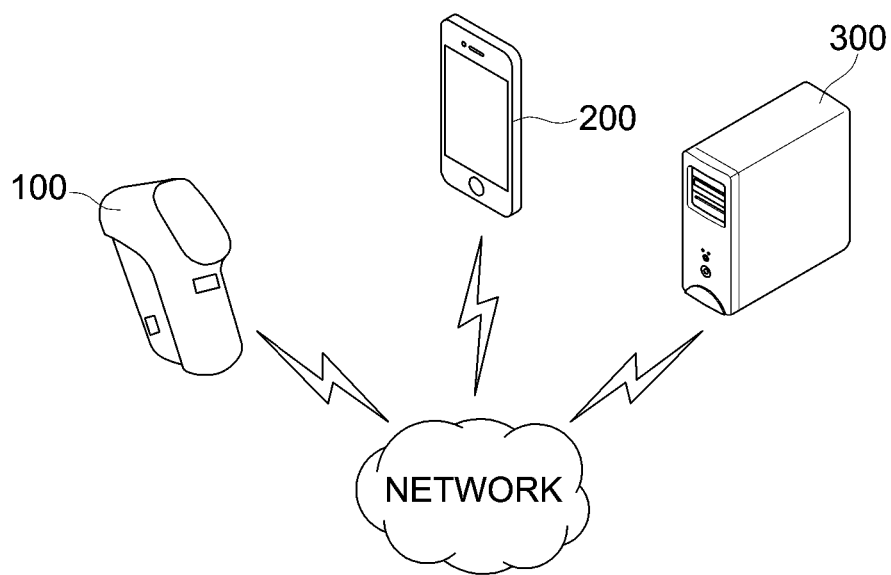
[FIG. 2]
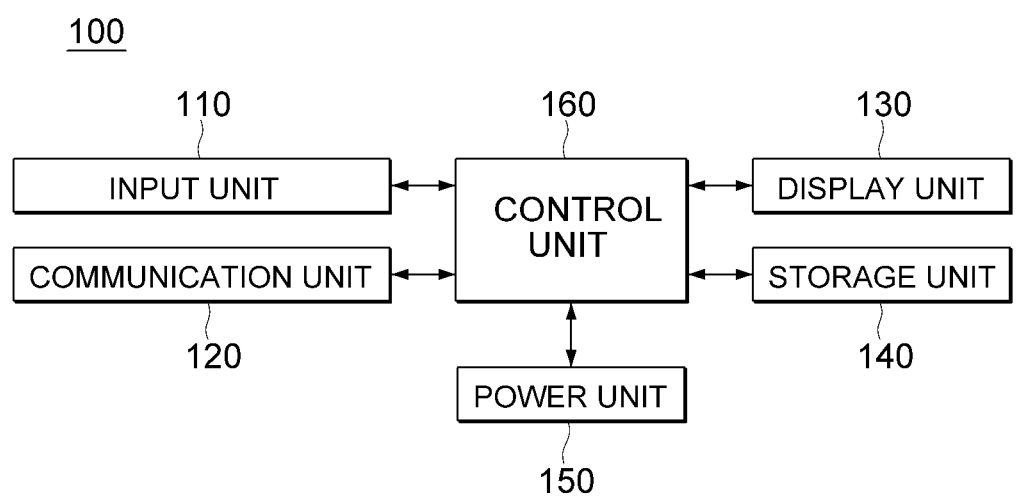

[FIG. 3A]
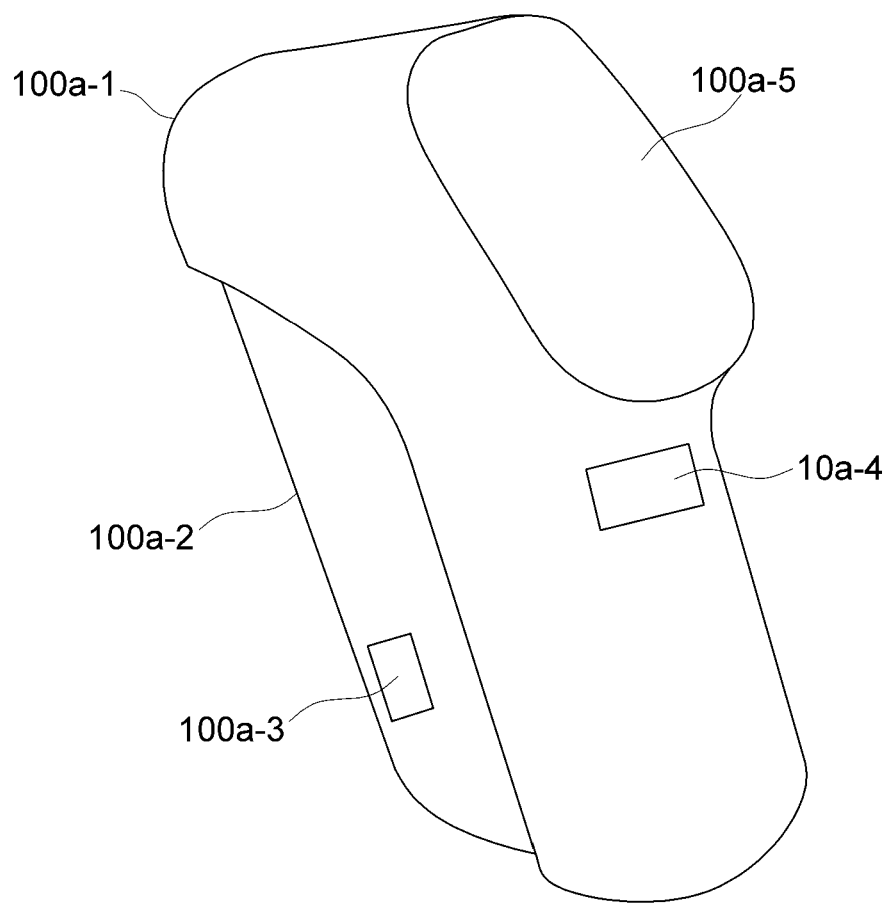

[FIG. 3B]
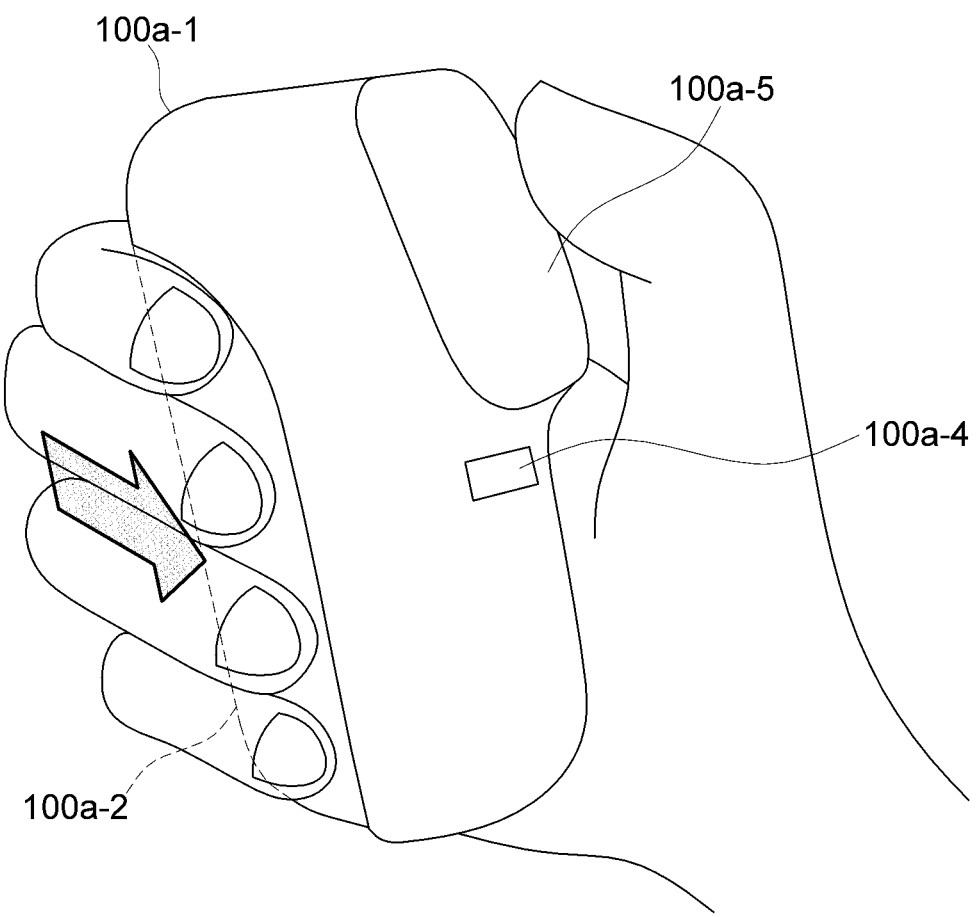

[FIG. 4]
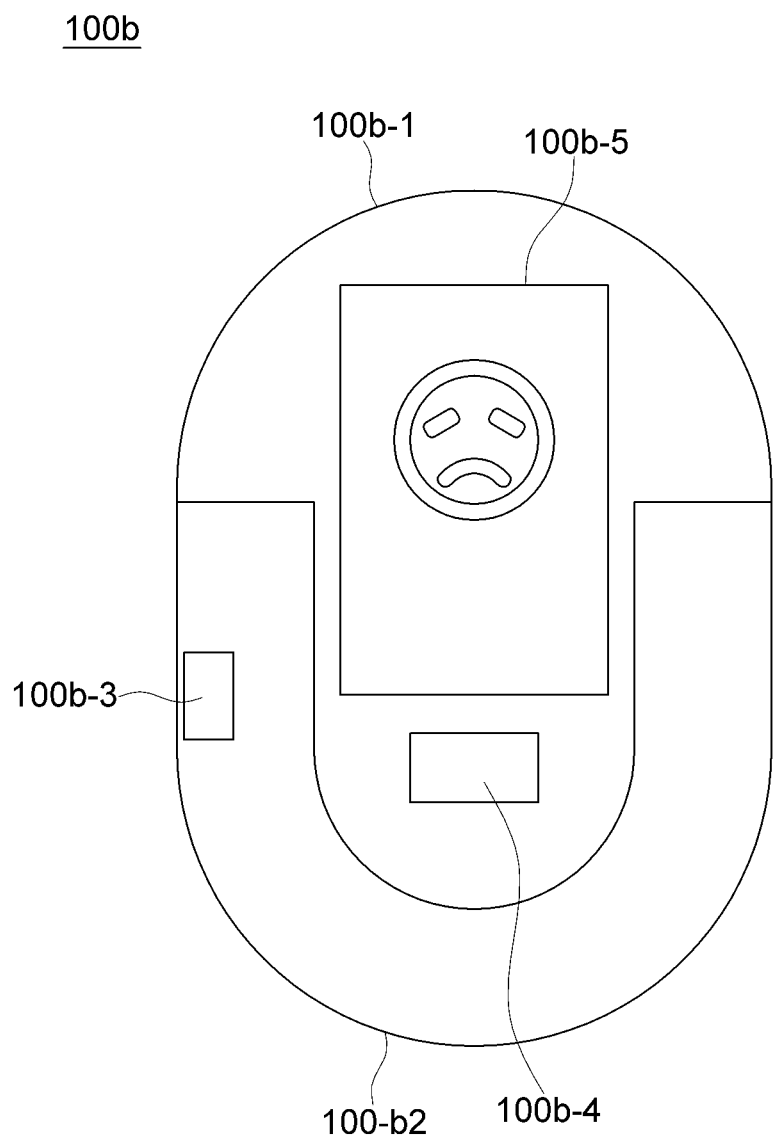

[FIG. 5A]
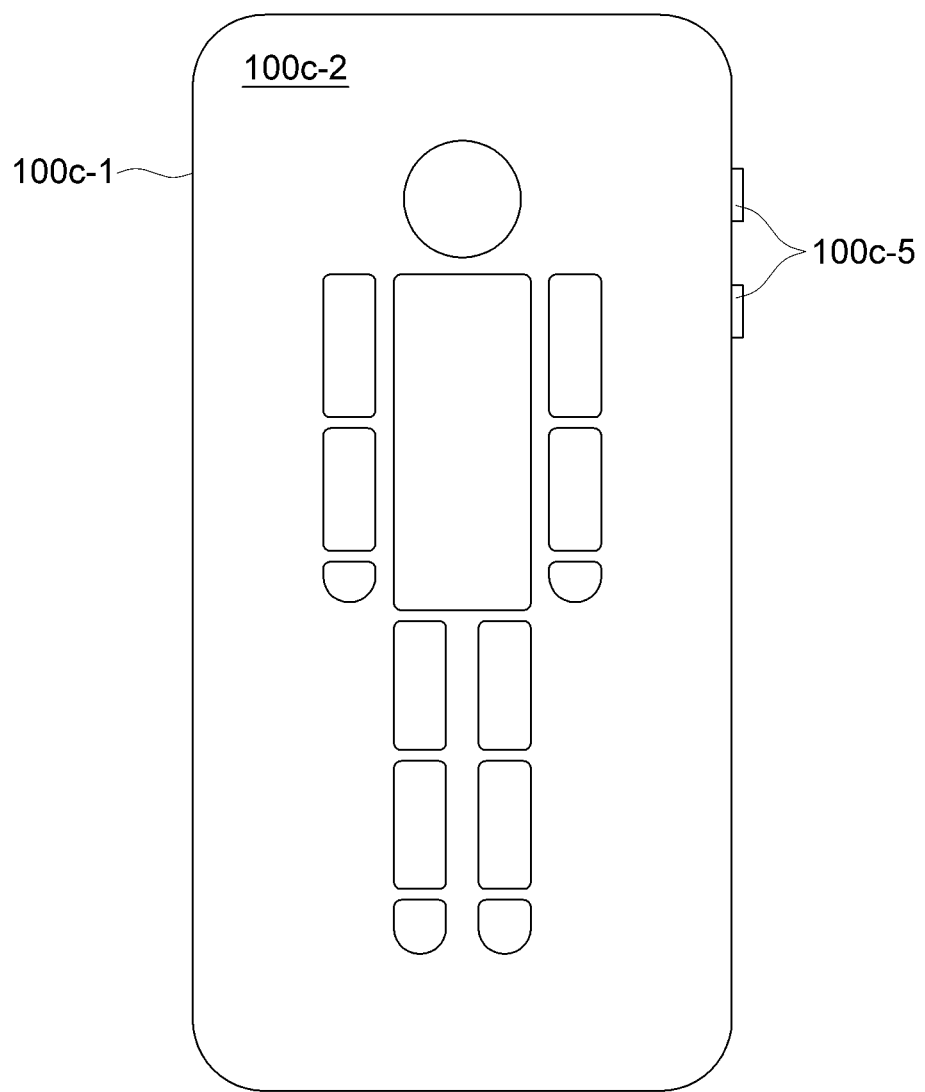

[FIG. 5B]
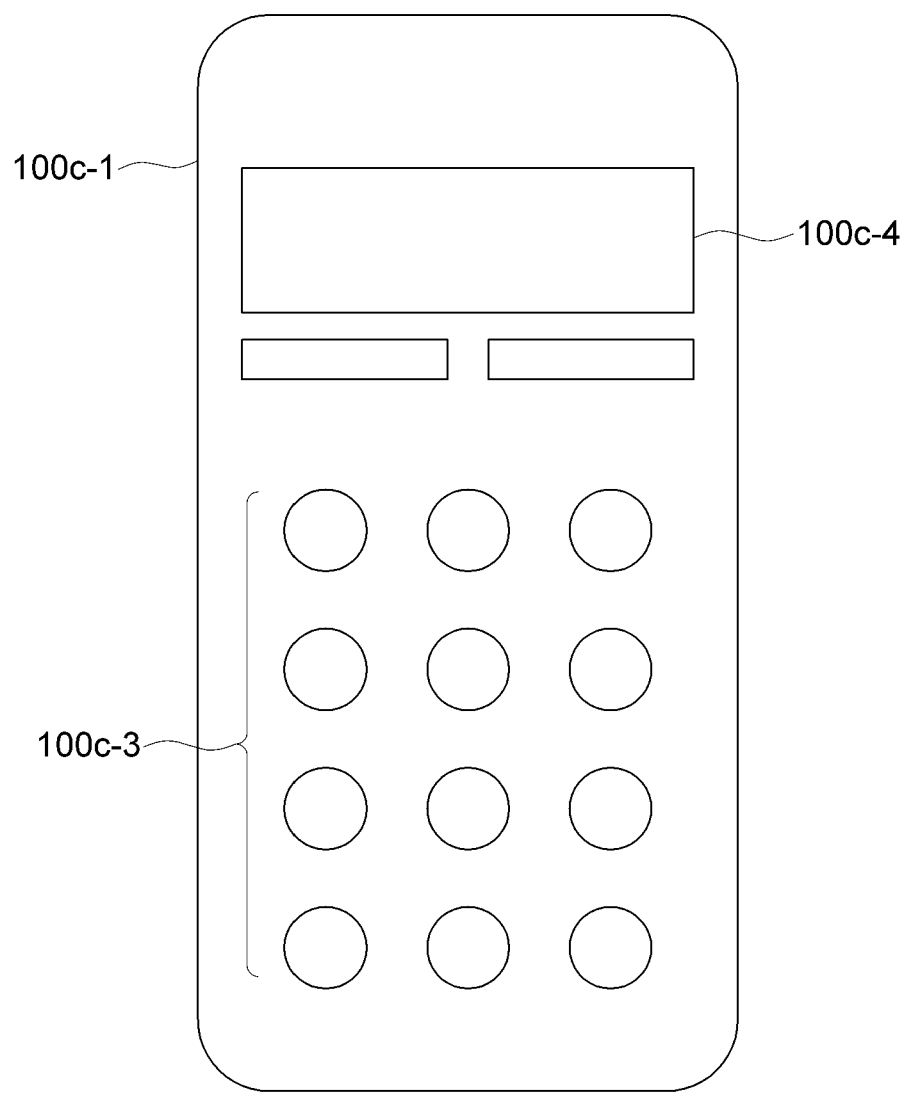

[FIG. 6]
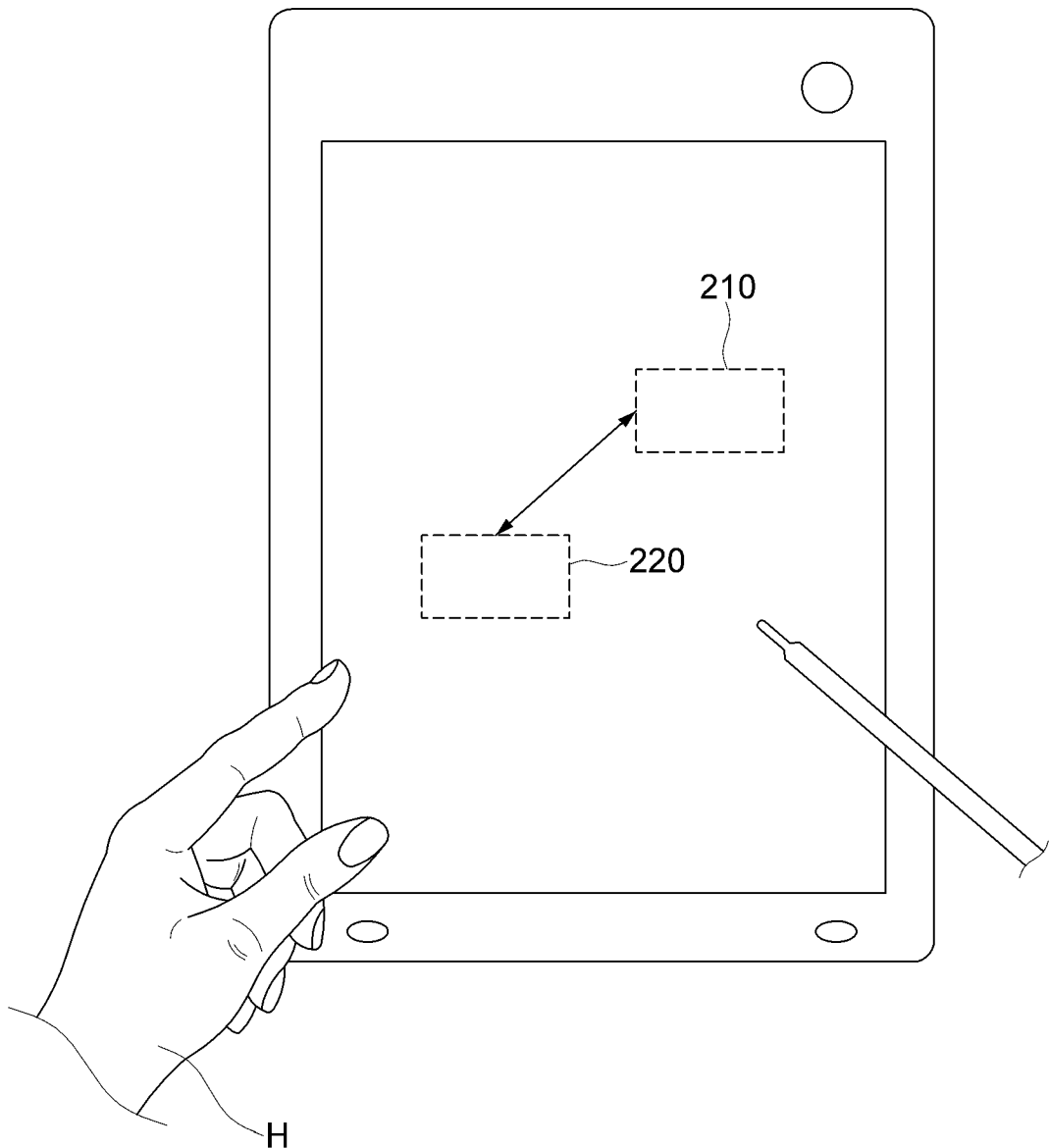

[FIG. 7]
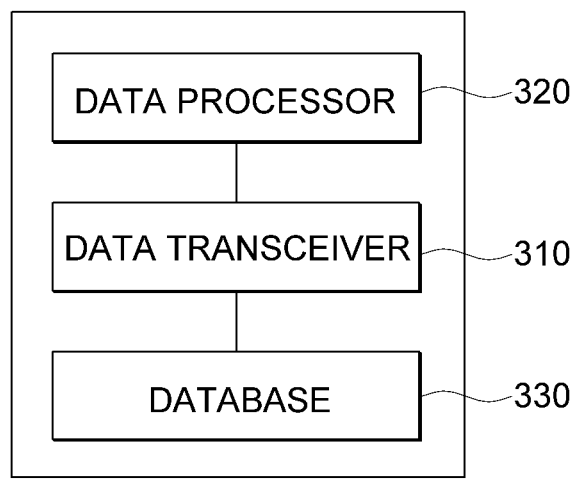

[FIG. 8]
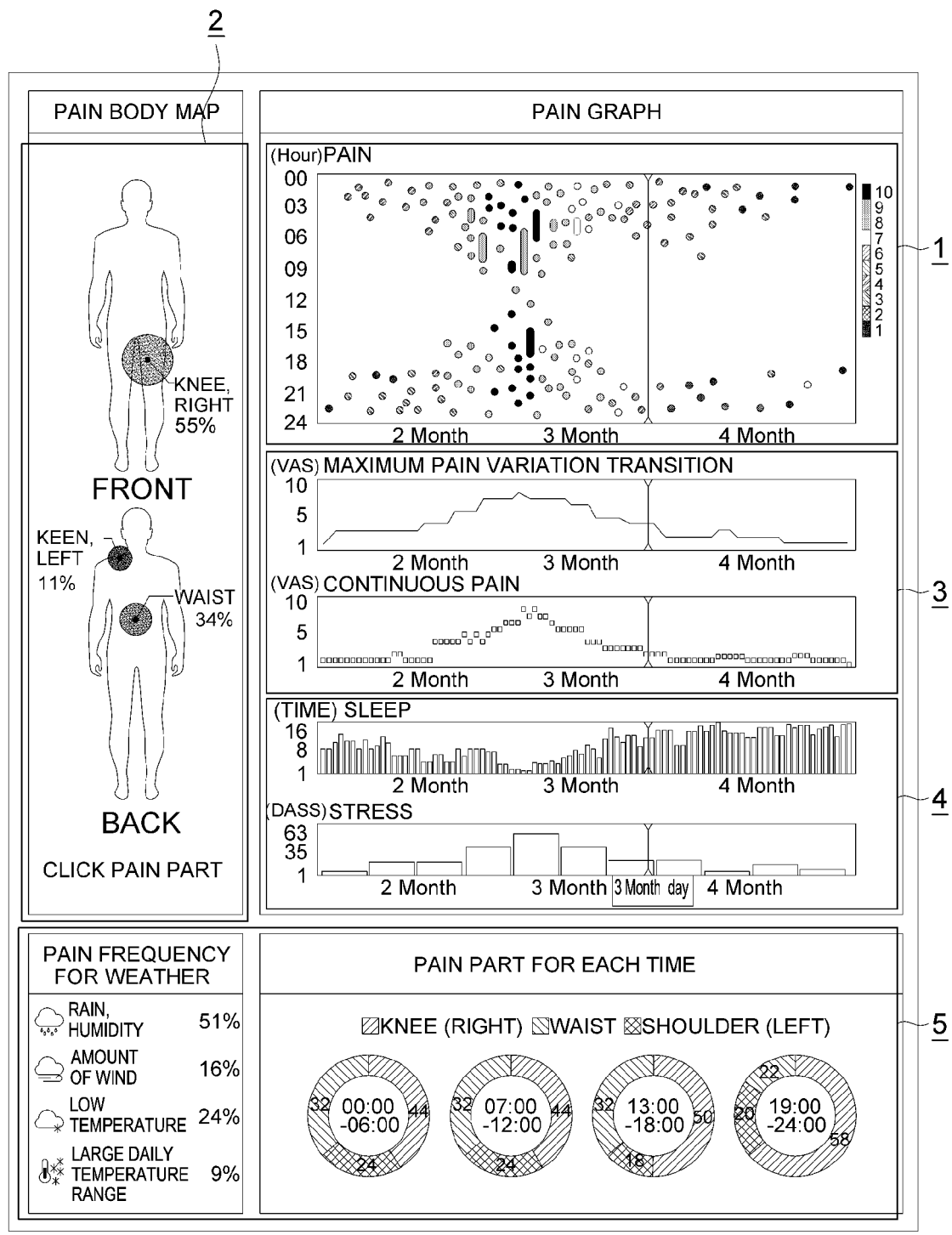

[FIG. 9]
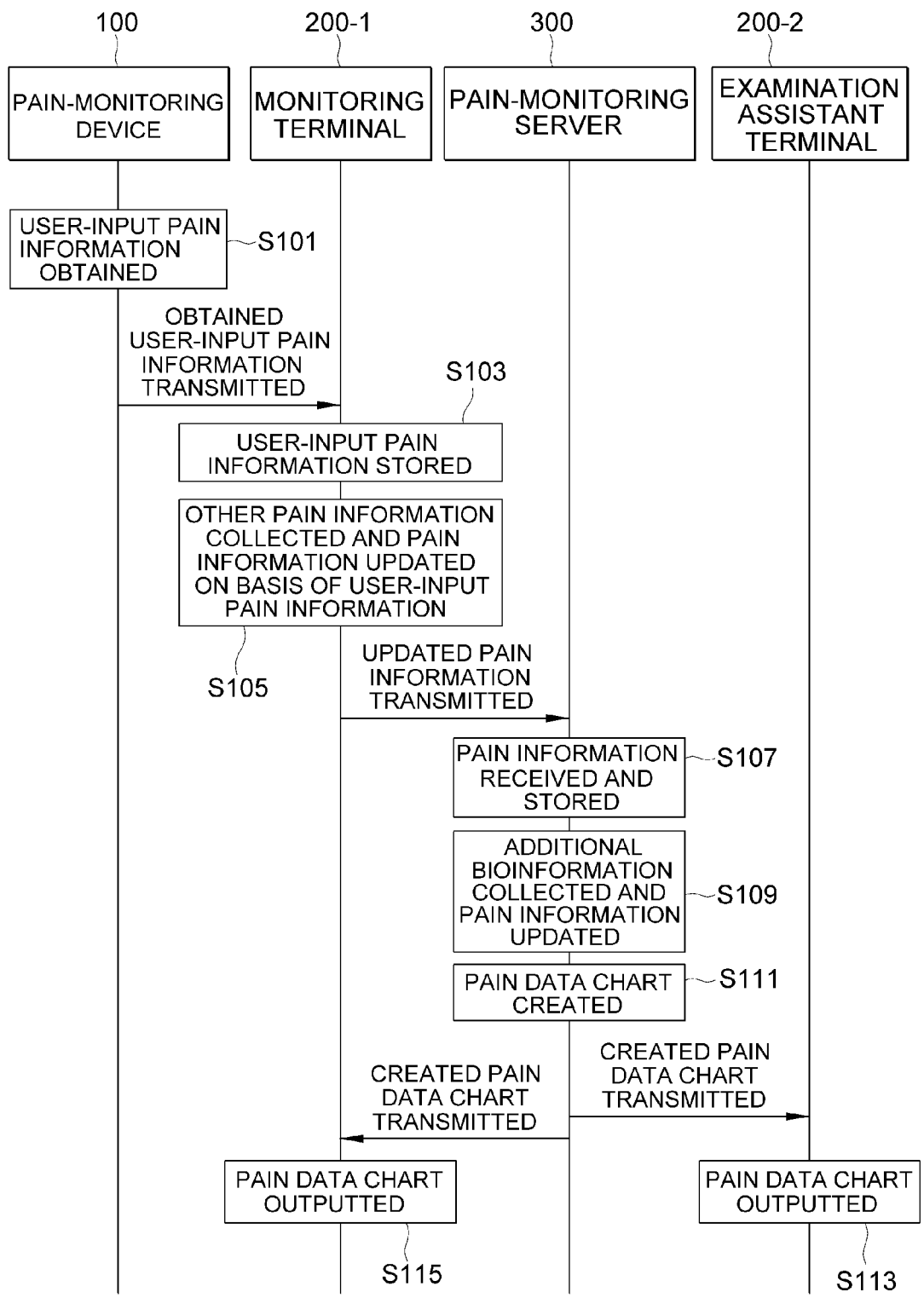

PAIN-MONITORING DEVICE AND METHOD

CROSS-REFERENCE TO RELATED APPLICATIONS

This application is the U.S. National Phase under 35 U.S.C. § 371 of International Application No. PCT/KR2019/009880 filed on Aug. 7, 2019, which in turn claims the benefit of Korean Application No. 10-2019-0055519 filed on May 13, 2019, the disclosures of which are incorporated by reference into the present application.

BACKGROUND OF THE DISCLOSURE

Field of the Disclosure

The present disclosure relates to pain-monitoring device and method. In detail, the present disclosure relates to pain-monitoring device and method that can obtain pain-related information by monitoring the pain of a patient, can quantify the obtained pain-related information, and can achieve patient-customized diagnosis on the basis of the pain-related information.

Related Art

A pain may be regarded as a kind of warning that shows sign for examination when the body is injured or a disease is generated. Accordingly, a process of objectively and accurately determine the reason of a pain may be a very important process of treating a diseased body.

Pains of the body are caused by various factors. For example, pains may be caused by the diseases of patient or inherent physical factors of patients such as patients' constitution, or may be caused by economical factors due to influence by the surrounding environment.

When a pain is caused of an inherent physical factor of a patient, a doctor can determine the reason of the patient in medical examination. However, it is limitative to find out continuous condition changes of a patient and pain-related information within the examination time between a doctor and the patient.

Further, when various items of pain-related information, such as the body part causing a pain of a patient, the degree of a patient, and additional physical problematic reactions due to a pain, are obtained only from the memory of the patient, there is a problem that reliability and objectivity in diagnosis of the patient are deteriorated.

Further, there is an environmental factor, a doctor depends on statement based on memory of a patient, so there is a problem that the doctor cannot accurately determine the reason of the pain due to distortion or errors in the memories. Further, there is a problem of medicinal misuse and abuse because medicines are prescribed on the basis of such physical and environmental factors.

Further, in order to increase the accuracy of tracing the factors of pains due to such physical/environmental factors, it is necessary to make a patient record physical/environmental factors using a specific recording tool when the patient feels sudden pains.

In relation to this, according to a prior art document 1, a tenderness measurement device that measures the depth of a pain by converting pressure applied by a user into an electrical signal has been disclosed. However, the tenderness measurement device of the prior art document 1 only simply measures a pain of a patient, so there is a technical limit in recognizing and taking appropriate follow-up measures against the pain. Further, the prior art document 1 still has a problem that not only the degree of a pain, but the physical information of a patient and environmental factors are not directly considered as the factors of the pain.

A device that inputs the intensity of a pain in real time through a wearable device has been disclosed in a prior art document 2. However, the prior art document 2 does not propose the configuration of a device for inputting various items of pain information required for diagnosis such as the intensity of a pain, the part of a pain, and the kind of a pain. That is, the prior art document 2 does not propose the configuration of a device that can quickly and easily input such various items of pain information in real time when a patient feels a pain. Further, the prior art document 2 does not propose a method for using pain information input by a patient for diagnosis.

Meanwhile, it is required to digitize/visualize obtained pain-related information in order to objectively find out invisible subjective information about a pain.

In detail, since current medial understanding of pains has difficulty in objectification and making a database, it is increasingly required to provide a system that can objectively determine pains of patients by introducing a technology that can clearly find out objective and relative references about individual pains.

In more detail, estimation of pains of patients depends on the memory of the patient even up to now using a Visual Analog Scale (VAS) is not more than one-off estimation. Due to this situation, there is a problem that it is difficult to find out the pattern, time, and relation with the environment of pain changes of patients, and relevance with the conditions of patients.

Further, patients who appeal various pains such as neuralgia, arthralgia, cancerous pain, vascular disease pain for a long period of time is increasing due to an explosive increase of chronic diseases. Further, other than these pains, pains due to surgery, operation, and medicines and various kinds of pains due to symptoms, acute diseases, etc. are increasing.

However, there is no system that can systematically classify and treat these various kinds of pains and a technology for this system is required.

Meanwhile, since pain-related information of patients is caused by various factors, it is required to generally monitor and systematically manage a plurality of pain-related data including pain-related information of patients and it is increasingly required to introduce a technology for the necessity.

SUMMARY OF THE DISCLOSURE

The present disclosure has been made in an effort to solve the problems in the related art described above and an object of the present disclosure is to provide an individual customized diagnosis/examination service that quantifies information about pains that patients feel by monitoring the pains of the patients that are generated in various situations, and that is fitted to the states of corresponding pains on the basis of the information.

Further, an object of the present disclosure is to provide pain-monitoring device and method that can effectively find out the state of a patient by obtain information about pains of a patient and generating visualized data on the basis of the information.

In detail, the present disclosure provides a pain-monitoring device that enables a patient who feels a pain to easily and intuitively input information about the pain.

Further, the present disclosure provides provide pain-monitoring device and method that improve accuracy of examination of a patient by generating and providing visualized information that objectively shows the pain state of the patient on the basis of pain-related information of the patient obtained through continuous monitoring.

A pain-monitoring device and method according to an embodiment of the present disclosure is a pain-monitoring device for obtaining information related to a pain of a user and providing a service of monitoring the pain of the user, includes: an input unit sensing pain-related input of the user; a display unit outputting pain-related information; and a control unit controlling the input unit and the display unit, in which the input unit includes: a touch input unit sensing touch input of the user; and a pressure measurement unit measuring pressure input of the user, and the control unit creates user-input pain information in accordance with the sensed pressure input and touch input.

In this case, the pressure measurement unit has a shape, which can be moved in accordance with a grip of a user, and includes an elastic member and a decompression sensor sensing pressure applied to the elastic member in accordance with the grip.

Further, the pain-monitoring device and method according to an embodiment of the present disclosure further include a body unit, in which the pressure measurement unit is disposed on a side of the body unit, and a touch screen including the touch input unit and the display unit is disposed on the body unit top.

Further, the pain-monitoring device and method according to an embodiment of the present disclosure further include a circular body unit, in which the pressure measurement unit is disposed on at least a portion of an outer circumference of the body unit, and a touch screen including the touch input unit and the display unit is disposed on the center of the body unit.

Further, the input unit includes a first input unit indicating a head, at least one second input unit indicating a body, at least one third input unit indicating a left arm, a least one fourth input unit indicating a right arm, at least one fifth input unit indicating a left leg, and at least one sixth input unit indicating a right leg.

Further, the pain-monitoring device and method according to an embodiment of the present disclosure further include a biosensor sensing input factors of the user.

Further, the input unit further includes a trigger button receiving input from the user for a temporal pain, and the control unit creates the user-input pain information when input through the trigger button is sensed.

Further, the control unit controls the display unit to display numbers according to intensity of pressure input through the pressure measurement unit and a pressing time, and determines a number determined in accordance with the intensity of the pressure as pain intensity.

Further, the control unit controls the display unit to gradually increase the displayed number in accordance with the pressing time, and determines a number displayed on the display unit as the pain intensity when the pressure becomes a predetermined number or less.

Further, the control unit controls the display unit to display a number according to the intensity of the pressure, corrects the displayed number in accordance with a change of the intensity of the pressure, and determines the number displayed on the display unit as the pain intensity when the pressure becomes a predetermined number or less.

Further, the control unit determines a change pattern of pain intensity in accordance with a change of the intensity of the pressure measured by the pressure measurement unit, and includes a change pattern of the determined pain intensity in the user-input pain information.

Further, the pain-monitoring device and method according to an embodiment of the present disclosure include a touch screen including the display unit and the touch input unit, in which the touch screen displays a graph image related to a pain body part, a pain type, additional abnormal reaction information, or a pain kind, and the control unit creates the user-input pain information in accordance with the touch input when the touch input for the graphic image is sensed.

Further, the pain-monitoring device and method according to an embodiment of the present disclosure is a pain-monitoring method in which a processor of an examination assistant terminal receiving user-input pain information obtained by a pain-monitoring device provides a pain-monitoring service, and the method includes: obtaining user-input pain information including pain intensity from the pain-monitoring device; sequentially accumulating and storing the user-input pain information, which is input a plurality of times, in pain information of the user; creating a pain data chart on the basis of the pain information; and outputting the created pain data chart.

In this case, the creating of a pain data chart on the basis of the pain information includes creating at least one or more of a main pain graph, a pain body map, a first relevant graph, a second relevant graph, and a third relevant graph on the basis of the pain information.

Further, the main pain graph is a graph showing the user-input pain information accumulated for a plurality of days as a heat map.

There is an effect that the pain-monitoring device and method according to an embodiment of the present disclosure monitors a pain of a patient that is generated in various situations, creates quantified data on the basis of the pain that the patient feels and information related to the pain, and provides an individual customized diagnosis/examination service for the corresponding pain on the basis of the data, thereby being able to achieve patient-customized diagnosis based on information obtained by quantifying/patterning the relationship between the pain of the patient and various factors related to the pain of the patient.

Further, there is an effect that the pain-monitoring device and method according to an embodiment of the present disclosure can more accurately sense the degree of a pain that a patient wants to input by standardizing the grade of a patient sensed on the basis of a grip in consideration of individual differences of grips obtained from patients.

Further, there is an effect that the pain-monitoring device and method according to an embodiment of the present disclosure can device a diagnosis result on the basis of more objective and accurate information when examining a patient by creating and providing information visualized on the basis of pain-related information of the patient obtained through continuous monitoring, thereby being able to improve the quality of patient examination and derive appropriate following measures.

Further, there is an effect that the pain-monitoring device and method according to an embodiment of the present disclosure can generally analyze and check a plurality of pain-related data by creating and providing information visualized using pain information including various items of pain-related information.

Further, there is an effect that the pain-monitoring device and method according to an embodiment of the present disclosure can overcome the problem of a diagnosis error and deterioration of objectivity that are generated when various items of pain-related information depends on only the memory of a patient by automatically obtaining pain-related data of a patient through a series of operations that are implemented in a pain-monitoring system.

Further, there is an effect that the pain-monitoring device and method according to an embodiment of the present disclosure can use even pain-related information that a patient has difficulty in inputting one by one by automatically collecting additional information related to a corresponding pain on the basis of pain information input by a patient.

Further, there is an effect that the pain-monitoring device and method according to an embodiment of the present disclosure can assist analysis of the pain state of a patient on the basis of a wider information and can improve objectivity of the analysis by providing visualized information for pain monitoring by using even pain-related information automatically collected, in addition to the pain information input by the patient.

Further, there is an effect that the pain-monitoring device and method according to an embodiment of the present disclosure can use a large amount of data, which makes it possible to find out what external factors have influenced a pain other than pain-related information, for pain examination by collecting additional bioinformation related to a patient from a device other than the pain-monitoring system.

Further, there is an effect that the pain-monitoring device and method according to an embodiment of the present disclosure makes it possible to more intuitionally and conveniently check the pain state of a patient by creating and providing visualized data using various graphs and charts on the basis of pain information of the patient.

Further, there is an effect that the pain-monitoring device and method according to an embodiment of the present disclosure can improve usability of visualized pain-related data through various interfaces by providing pain information of a patient through medical council assistant contents and/or medical council contents, can contributes effective understanding by intuitionally recognizing the pain state of a patient, and can improve the quality of examination through pain monitoring.

Further, there is an effect that the pain-monitoring device and method according to an embodiment of the present disclosure can improve the quality of general life of a patient in addition to disease management of the patient by monitoring and managing changes of a pain and changes of symptoms of the patient, can efficiently adjust use of medicines that is applied to the patient, can find out early and prevent complications that may generated in the patient, and correspondingly can reduce social-medical costs.

Further, there is an effect that the pain-monitoring device and method according to an embodiment of the present disclosure can contribute achieve industrialization based on development and copyrighting of an algorithm through construction of big data by monitoring and managing changes of a pain and changes of symptoms of a patient using quantified data.

However, effects that can be obtained in the present disclosure are not limited to the effects stated above, and other effects not stated can be clearly understood from the following description.

BRIEF DESCRIPTION OF THE DRAWINGS

FIG. 1 is a conceptual diagram of a pain-monitoring system according to an embodiment of the present disclosure.

FIG. 2 is a block diagram of the inside of a pain-monitoring device according to an embodiment of the present disclosure.

FIG. 3A is an example schematically showing the external appearance of the pain-monitoring device according to an embodiment of the present disclosure.

FIG. 3B is a diagram illustrating the operation principle of a pain-monitoring device according to an embodiment of the present disclosure.

FIG. 4 is an example schematically showing the external appearance of a pain-monitoring device according to another embodiment of the present disclosure.

FIG. 5A and FIG. 5B are examples schematically showing the external appearance of a pain-monitoring device according to another embodiment of the present disclosure.

FIG. 6 is an example showing a terminal according to an embodiment of the present disclosure.

FIG. 7 is a block diagram of the inside of pain-monitoring server according to an embodiment of the present disclosure.

FIG. 8 is an example of a pain data chart according to an embodiment of the present disclosure.

FIG. 9 is a flowchart illustrating a pain-monitoring method using a pain-monitoring device according to an embodiment of the present disclosure.

DESCRIPTION OF EXEMPLARY EMBODIMENTS

The present disclosure may be modified in various ways and implemented by various exemplary embodiments, so that specific exemplary embodiments are shown in the drawings and will be described in detail herein. The advantages and features of the present disclosure, and methods of achieving them will be clear by referring to the exemplary embodiments that will be describe hereafter in detail with reference to the drawings. However, the present disclosure is not limited to the disclosed embodiments and may be implemented in various ways. In the following embodiments, terms such as "first" and "second" are used to discriminate a component from another component without limiting the components. Further, singular forms are intended to include plural forms unless the context clearly indicates otherwise. Further, terms such as "include" or "have" mean that the features or components described herein exist without excluding the possibility that one or more other features or components are added. Further, components may be exaggerated or reduced in size for the convenience of description. For example, the sizes and thicknesses of the components shown the figures are selectively provided and the present disclosure is not necessarily limited thereto.

Hereinafter, embodiments of the present disclosure are described in detail with reference to the accompanying drawings, and in the following description of the accompanying drawings, like reference numerals are given to like components and repetitive description is omitted.

FIG. 1 is a conceptual diagram of a pain-monitoring system according to an embodiment of the present disclosure.

Referring to FIG. 1, a pain-monitoring system according to an embodiment of the present disclosure may include a pain-monitoring device, a terminal 200, and a pain-monitoring server 300.

The components shown in FIG. 1 may be connected through a network. The network means a connection structure enabling information exchange among nodes such as the pain-monitoring device, the terminal 200, and the pain-monitoring server 300. For example, the network may include a 3GPP (3rd Generation Partnership Project) network, an LTE (Long Term Evolution) network, a WIMAX (World Interoperability for Microwave Access) network, the internet, a LAN (Local Area Network), a Wireless LAN (Wireless Local Area Network), a WAN (Wide Area Network), a PAN (Personal Area Network), a Bluetooth network, a satellite broadcasting network, an analogue broadcasting network, a DMB (Digital Multimedia Broadcasting) network, etc., but is not limited thereto.

Hereafter, a patient in an embodiment of the present disclosure may be a person who is expected to have a pain, a person who has experienced a continuous or intermittent pain, and a person who needs to check the degree of reduction of a pain in the process of treatment.

Further, the patient may generate pain information busing the pain-monitoring device when a pain is generated.

The pain information according to the present disclosure is information about a pain of a patient and may include 1) user-input pain information, 2) other pain information, and 3) additional bioinformation.

In detail, the user-input pain information is pain-related information input through the pain-monitoring device 100 and/or the terminal 200 from a patient and may be information including at least one or more of pain body part information that is information about a body part where a pain is generated, pain intensity information showing the intensity of a pain, pain pattern information related to the cycle of a pain, pain type information, pain kind information, and additional abnormal reaction information.

The pain type is information about the types of senses of pain. For example, when the sense of pain is 'cold', a 'tooth' type may be provided as a pain type, and as another example, when the sense of pain is 'sting', a 'stomachache' may be provided as a pain type.

Further, the pain types may be determined and provided on the basis of categories such as somatic pain, visceral pain, or neuropathic pain.

Further, the pain kind may be any one of nociceptive, inflammatory, neuropathic, and functional pains.

Further, the additional abnormal reaction information, which is information about a physical abnormal reaction that accompanies a patient when a pain is generated, may be information about symptoms such as a feeling of vomiting, a vertigo, depression, fatigue, pyrexia, and/or convulsions. Next, the other pain information, which is information that is automatically added and collected by the pain-monitoring system on the basis of the user-input pain information, may be information including at least one of pain cycle information, pain generation time information, and patient-surrounding environment information (temperature, humidity, weather, and/or location).

The pain cycle information may be information showing the cycle of a pain such as whether a pain of a patient is a continuous pain that is continuous generated or a sudden pain that is temporarily generated.

The pain cycle information may be obtained on the basis of pain pattern information obtained from a patient.

The other pain information is collected on the basis of the user-input pain information and added to the pain information of the patient, whereby the pain information can be updated.

The additional bioinformation, which is patient-related bioinformation that is obtained from a device of other than the pain-monitoring system, may be information including at least one of sleep and stress index information.

The additional bioinformation is collected from an external device and added to the pain information of a patient, whereby the pain information can be updated.

Hereafter, before a pain-monitoring method using the pain-monitoring device 100 according to an embodiment of the present disclosure is described, the components included in the pain-monitoring system are described in detail.

Pain-Monitoring Device

First, the pain-monitoring device 100 according to an embodiment of the present disclosure may be a device that obtains, records, and provides information about various pains that are generated from a patient.

The pain according to an embodiment of the present disclosure includes not only a simple painful symptom, but various symptoms such as all of cardiovascular symptoms (arrhythmia, gear acceleration, palpitation, etc.), respiratory symptoms (dyspnea, etc.) gastrointestinal disorders (pyrosis, vomiting, nausea, dysphagia, etc.), neurological symptoms (vertigo, etc.), psychopathic symptoms (suicidal thought, uneasiness, etc.), and urinary symptoms (dysuria, urinary frequency, etc.)

In detail, the pain-monitoring device 100 can obtain user-input pain information on the basis of input by a user.

As an embodiment, the pain-monitoring device 100 can obtain user-input pain information related to a patient by sensing pressure input or touch input from the patient.

In this case, the pain-monitoring device 100 can determine paint intensity (a pain grade) showing the degree of a pain that the patient wants to input on the basis of pressure input obtained from the patient.

When the pain-monitoring device 100 determines a pain grade on the basis of pressure input by a grip of a patient, the pain-monitoring device 100 may perform pain grade calibration for standardizing individual pain grades on the basis of grips obtained from patients to select accurate pain grades in consideration of individual differences of the grips of the patients.

In detail, when the pain-monitoring device 100 is initially resets, the pain-monitoring device 100 may perform pain grade calibration for setting a patient-customized standardized pain grade. Further, the pain-monitoring device 100 may perform pain grade calibration when user change or re-registration is performed on an application for a pain-monitoring service of the terminal 200 that operates with the pain-monitoring device 100 or when the configuration of the pain-monitoring device 100 is reset and/or the configuration of the application is reset.

In order to perform pain grade calibration, the pain-monitoring device 100 can measure first a maximum grip value when an input unit for a patient to input the degree of a pain as pressure into the pain-monitoring device 100 is most strongly held. In this case, the pain-monitoring device 100 can measure the maximum pressure value at least twice or more for accurate measurement.

Further, the pain-monitoring device 100 can set a predetermined pressure value corresponding to the maximum pain grade by matching the measured maximum pressure value to the maximum pain grade showing the maximum degree of pain of a plurality of pain grades.

For example, when it is configured that pain grades are composed of grades 1 to 10 and a pain increases as it goes to the grade 10, the pain-monitoring device 100 can set a pressure value for the maximum pain grade by matching the maximum pressure value measured from a patient to the grade 10.

Further, the pain-monitoring device 100 can set predetermined pressure values matched to the other lower pain grades except for the maximum pain grade on the basis of the measured maximum pressure value. In detail, the pain-monitoring device 100 can set pressure values matched to the other lower pain grades by performing reverse operation for the lower pain grades on the basis of the maximum pressure value.

For example, when the pain grades are composed of grades 1 to 10 and the maximum pressure value is matched to the grade 10 that is the maximum pain grade, the pain-monitoring device 100 can perform sequential reverse operation from the grade 10 to the other lower pain grades 9 to 1 on the basis of the maximum pressure value that is the pressure value for the grade 10. Further, the pain-monitoring device 100 can set a pressure value for each pain grade by matching the input value obtained through reverse operation for each grade to each grade In detail, for example, when it is configured that the maximum pressure value 10 is matched to a pressure value for the grade 10 that is the maximum pain grade and reverse operation for applying −1 is performed on each grade, the pain-monitoring device 100 can set a pressure value for each pain grade, that is, a pressure value of 9 for the grade 9, a pressure value of 8 for the grade 8, a pressure value of 7 for the grade 7, . . . and a pressure value of 1 for the grade 1.

As described above, the pain-monitoring device 100 sets and uses a pain grade optimized for a patient by standardizing a plurality of pain grades on the basis of the maximum pressure values when patients apply the largest grips, thereby being able to provide a pain-monitoring service on the basis of more accurate data for individual patients.

Although it was described above that the pain-monitoring device 100 performs pain grade calibration for standardizing patient-customized pain grades, various embodiments in which the terminal 200 and/or the pain-monitoring server 300 may be possible, depending on embodiments.

Further, the pain-monitoring device 100 can create quantified and/or imaged pain-related information on the basis of obtained user-input pain information, and can provide the generated information through a display.

Further, in an embodiment of the present disclosure, the pain-monitoring device 100 can provide an SOS call function for serious cases or people with inconvenient movement.

In detail, the pain-monitoring device 100 can provide an SOS call function of requiring an emergency call on the basis of the pain-monitoring device 100, an application of performing an SOS-related function in cooperation with the pain-monitoring device 100, and/or GPS information obtained by the pain-monitoring device 100 when a patient is in an emergency Meanwhile, the pain-monitoring device 100 may be a device registered on the terminal 200. The pain-monitoring device 100 may be registered on the terminal 200 by inputting an identification number or a barcode of the pain-monitoring device 100 into an application installed in the terminal 200.

Further, the terminal 200 and/or the pain-monitoring server 300 according to an embodiment of the present disclosure can manage the pain-monitoring device 100.

In another embodiment, the pain-monitoring device 100 includes even the configuration of the terminal 200 and can provide a pain-monitoring service by performing direct data communication with the pain-monitoring server 300.

FIG. 2 is a block diagram of the inside of the pain-monitoring device according to an embodiment of the present disclosure.

Referring to FIG. 2, the pain-monitoring device 100 may include an input unit 110, a communication unit 120, a display unit 130, a storage unit 140, a power unit 150, and a control unit 160.

First, the input unit 110 can sense various items of input from a patient which are related with a pain-monitoring service.

In detail, in terms of structure, the input unit 110 may include 1) a touch input unit and/or 2) a pressure measurement unit.

First, the touch input unit according to an embodiment of the present disclosure may be implemented as a touch screen in which a display and an input unit are combined, and can get input of user-input pain information related to a pain from a patient.

As an embodiment, the touch input unit can get input of information about a pain body part, a pain type, and/or a pain kind of a patient from the patient. For example, the touch screen can provide a user interface for inputting a pain body part by providing a graphic image showing body parts to enable touch selection. Sequentially, the touch screen can provide a user interface for inputting a pain type by providing a graphic image showing pain types to enable touch selection. Further, the touch screen can provide a user interface for inputting a pain kind by providing a graphic image showing pain kinds to enable touch selection.

Further, the pressure measurement unit according to an embodiment of the present disclosure can obtain user-input pain information that is information about a pain of a patient on the basis of pressure input that is input from the patient.

In detail, the pressure measurement unit may be implemented in at least one or more types of 1) a grip sensing type, 2) a decompression touch type, 3) a wheel type, and 4) a button type.

In more detail, first, a pressure measurement unit of a grip sensing type includes a pressure measurer decompression sensor that measures pressure and can measure the intensity of pressure and/or the application time of pressure that is applied when a patient holds the pressure measurement unit by hand. Further, it is possible to determine the intensity of a pain input by a user (the grade/unit of a pain) in accordance with the measured intensity of pressure and/or application time of pressure.

That is, when the pressure measurement unit of a grip sensing type measures the intensity of pressure applied by a user, the intensity of a pain can be input in proportion to the measured intensity of pressure. Further, when the pressure measurement unit of a grip sensing type measures the time of pressure applied by a user, the intensity of a pain can be input in accordance with the measured pressure time.

In an embodiment, when a grip of a user is measured, the control unit 160 can control the display unit 130 to gradually increase and display the number of pain intensity and can determine the pain intensity number displayed when the grip of the user is removed as the pain intensity presently applied to the user.

Further, in an embodiment, the control unit 160 can diagram a change of a grip and a change of a pain even during pain duration time by transmitting the intensity of a grip according to an increase and a decrease of the grip for a time for which the pain continues, in addition to when the grip is removed.

In this case, the control unit 160 can assist the user to quickly and intuitionally input the intensity of a pain that he/she feels by changing the increasing speed of the pain intensity number in proportion to the measured intensity of a grip.

Further, when a pain is temporarily generated without continuing (e.g., arrhythmia), the control unit 160 can get input of pressure through a handle to which a grip is applied or another additional button operation.

In another embodiment, the control unit 160 can display a number proportioned to the intensity of a grip of a user on the display unit 130 and can determine the number as the pain intensity presently applied to the user. Further, control unit 160 can change the number through a change of the intensity of a grip input by the user, and thus, can change the pain intensity.

In this case, changes of a color and a facial expression that depend on the intensity of a pain are both displayed on the display unit 130 of the pain-monitoring device 100 so that the degree of the pain can be intuitionally recognized.

The pressure measurement unit of a grip sensing type can sense a change pattern of pain intensity by continuously sensing a change of the intensity of pressure. That is, when a user has a continuous pain, the user inputs the pain duration time and a change of the pain, which he/she feels, through the pressure measurement unit of a grip sensing type while continuously changing the intensity of the grip, thereby being able to input the duration time of the pain and the change pattern of the pain intensity. The control unit 160 can determine the type of the pain or the pain cycle even without specific input on the basis of the change pattern of pain intensity input in this way.

Further, the pressure measurement unit of a grip sensing type can perform initial grip setting because users may have different intensity of grips. For example, initial setting may be performed to get input of a maximum grip or/and a minimum grip that a user can apply and to determine the pain intensity in accordance with the input pressure value.

Further, the grip measurement unit of a decompression touch type may be implemented in a type in which a decompression touch sensor is combined with a touch panel, and can measure the intensity of a pain by sensing pressure and/or time of a touch on the grip measurement unit of a decompression sensing type by a patient for inputting information about the pain.

Further, the grip measurement unit of a wheel type can measure the intensity of a pain in accordance with movement (e.g., rotation and inclination) of a wheel that is controlled by a patient.

For example, the grip measurement unit of a wheel type can obtain pain intensity of a patient by increasing the intensity of a pain when the wheel is rotated right by the patient and decreasing the intensity of a pain when the wheel is rotated left.

Further, the grip measurement unit of a button type can measure the intensity of a pain by sensing pressure and/or time that is input to the grip measurement unit of a button type by a patient for inputting information about the pain.

For example, the grip measurement unit of a button type may provide a plurality of buttons that provide number from 0 to 9, respectively, and can obtain the intensity of a pain by sensing pressure that is applied to one or more of the plurality of provided buttons and time for which the pressure is applied.

Further, the grip measurement unit may measure the degree of a pain on the basis of not only a decompression grip type, but the intensity of tension for pulling a button.

Further, the grip measurement unit may collect pain data for each pain part by attaching a sensor and/or a device that can input a pain in a touch type and by receiving a pain by receiving touch input through the sensor.

Meanwhile, in terms of function, the input unit 110 may include at least one or more of 1) a pain part input unit, 2) a pain intensity input unit, 3) a pain type input unit, 4) a pain kind input unit, and 5) an other input unit.

In detail, the pain part input unit can get input of what part of the patient body a pain has been generated at, from the patient.

Further, the pain intensity input unit can get input of the intensity (grade, unit) of a pain generated from a patient, that is, strength/weakness information of a pain.

Further, the pain type input unit can get input of information about a pain sense type for a pain generated in a patient.

Further, the pain type input unit can get input of information about a pain kind (e.g., a nociceptive pain, an inflammatory pain, a neuropathic pain, and a functional pain) of a pain generated in a patient.

Further, at least one of the pain type input unit and the pain kind input unit may get input of additional abnormal reaction information of a patient.

In detail, one of the pain type input unit and the pain kind input unit can obtain additional abnormal reaction information of a patient by sensing input of the patient providing information about at least one or more of symptoms such as a feeling of vomiting, a vertigo, depression, fatigue, pyrexia, and/or convulsions.

Further, the other input unit can get input of other pain-related information about a pain of a patient other than the pain part, the pain intensity, the pain type, or the pain kind described above.

In an embodiment, the other input unit may include a trigger button that can get input about a peak pain that a patient instantaneously feels, and/or a biosensor that can determine whether input from a patient is correct or wrong input. Next, the communication unit 120 can transmit/receive various data and/or information for a pain-monitoring service.

As an embodiment, the communication unit 120 can transmit/receive data related to a pain-monitoring service (e.g., user-input pain information) by communicating with the terminal 200 and/or the pain-monitoring server 300.

Further, in an embodiment, the communication unit 120 can perform data transmission to the pain-monitoring server 300 by transmitting data to the monitoring terminal 200 or by transmitting data to the pain-monitoring server 300 using the monitoring terminal 200 through 1) near field communication (e.g., Bluetooth, WiFi (Wireless Fidelity)), and can also perform direct data transmission to the pain-monitoring server 300 through 2) remote communication (e.g., WAN (Wide Area Network).

Further, the communication unit 120 can obtain location information about a pain-monitoring device 100 when a patient inputs a pain through the pain-monitoring device 100 using at least one or more of 3) GPS, GLONASS, and other navigation systems.

The communication unit 120 obtaining the location information of the pain-monitoring device 100 can provide the obtained location information to the terminal 200 and/or the pain-monitoring server 300 through a network.

The communication unit 120 can transmit/receive wireless signals to/from at least one of a base station, an external terminal 200, and a certain server on a mobile communication network constructed in accordance with technical standards or communication methods for mobile communication (e.g., GSM (Global System for Mobile communication), CDMA (Code Division Multi Access), HSDPA (High Speed Downlink Packet Access), HSUPA (High Speed Uplink Packet Access), LTE (Long Term Evolution), and LTE-A (Long Term Evolution-Advanced)).

Next, the display unit 130 can output various items of information related to a pain-monitoring service as a graphic image.

As an embodiment, the display unit 130 can output and provide user-input pain information including a pan body part, pain intensity, a pain type, and/or a pain kind according to pressure input of a patient as a graphic image.

In this case, the display unit 130 can output information about a pain of a patient using numbers and/or symbolic icon images (e.g., a facial expression icon).

That is, the display unit 130 can create and output a graphic image through which pain-related information of a patient can be more intuitionally recognized.

The display unit 130 may include at least one of a liquid crystal display (LCD), a thin film transistor liquid crystal display (TFT LCD), an organic light emitting diode (OLED), a flexible display, a 3D display, and an e-ink display.

Further, when the input button is a touch type, a touch panel for implementing the input button may be disposed in the display unit 130.

Such a touch panel may be any type in which a display panel and a touch panel are combined such as an in-cell type and an on-cell type.

Next, the storage unit 140 can store any one or more of various application programs, applications, data, and commands for providing the pain-monitoring service according to an embodiment of the present disclosure.

As an embodiment, the storage unit 140 can store and manage user-input pain information, other pain information, additional bioinformation, an identification number, and/or patient identification information, etc.

The storage unit 140 may be various storage devices such as a ROM, a RAM, an EPROM, a flash drive, a hard drive, and may be a web storage that performs the storage function of the storage unit 140 on the internet.

Next, the power unit 150 can supply power for activating the pain-monitoring device 100 to each component by receiving external power and/or internal power under control by the control unit 160.

For example, the power unit 150 may include at least any one or more of a battery, a connection port, a power supply controller, and a charger.

Finally, the control unit 160 can control general operation of the components described above to provide the pain-monitoring service.

Meanwhile, various embodiments described herein, for example, may be implemented in a recording medium that can be read out through a computer or similar devices using hardware, software, or a combination thereof.

According to hardware implementation, embodiments described herein can be realized using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and electric units for executing other functions. In some cases, such embodiments may be implemented by the control unit 160.

According to software implementation, embodiments such as a procedure or a function may be implemented with a separate software module that causes execution of at least one function or operation. A software code may be implemented by a software application read in an appropriate program language. The software code may be stored in the storage unit 140 and may be executed by the control unit 160.

Hereafter, the pain-monitoring device 100 that implements the pain-monitoring service is described in more detail.

FIG. 3A is an example schematically showing the external appearance of the pain-monitoring device according to an embodiment of the present disclosure, FIG. 3B is a diagram illustrating the operation principle of the pain-monitoring device according to an embodiment of the present disclosure, and FIG. 4 is an example schematically showing the external appearance of a pain-monitoring device according to another embodiment of the present disclosure.

First, referring to FIGS. 3A and 3B, a first pain-monitoring device 100a according to an embodiment of the present disclosure may be a pain-monitoring device implemented in a dynamometer suitable for applying pressure (i.e., a grip) by holding by hand on the basis of a body-contact design.

Further, referring to FIG. 4, a second pain-monitoring device 100b according to another embodiment of the present disclosure may be implemented in a dynamometer type having a gravel stone shape that is suitable for applying pressure by holding by hand.

In this case, the first pain-monitoring device 100a and the second pain-monitoring device 100b have a difference in terms of external appearance, but are the same in that they are implemented in a handy type that can be carried by hand or can be received in consideration of usability of a patient. Further, the first pain-monitoring device 100a and the second pain-monitoring device 100b may be implemented in a type considering the curvature of a human body in operation in order to improve usability of various pain-monitoring devices.

Further, the first pain-monitoring device 100a and the second pain-monitoring device 100b may be the same in the functional configuration according to each component, that is, the functional characteristics that the first and second pain-monitoring devices 100a and 100b perform except for the external appearance.

Hereafter, each component constituting the first pain-monitoring device 100a and the second pain-monitoring device 100b is described in detail.

In an embodiment, the first and second pain-monitoring devices 100a and 100b may include body units 100a-1 and 100b-1, pressure measurement units 100a-2 and 100b-2, biosensors 100a-3 and 100b-3, trigger buttons 100a-4 and 100b-4, and touch screens 100a-5 and 100b-5.

First, the body units 100a-1 and 100b-1 form the external appearance of the first and second pain-monitoring devices 100a and 100b and may be equipped with/include various units for activating the pain-monitoring devices inside and outside.

Next, the pressure measurement units 100a-2 and 100b-2 can sense pressure (grip) input that is applied from a patient, and can obtain the time for which pressure is applied.

In this case, the first and second pain-monitoring devices 100a and 100b including the pressure measurement units 100a-2 and 100b-2 can obtain pain intensity and/or pain pattern information that is user-input pain information on the basis of the obtained pressure and/or pressing time.

Further, the pressure measurement units 100a-2 and 100b-2 may include pressure measurer decompression sensors and biosensors the 100a-3 and 100b-3.

In this case, the pressure measurer decompression sensors can measure the degree of a grip according to pressure input of a patient and can obtain a time for which the grip is applied.

Further, the biosensors 100a-3 and 100b-3 can determine whether the pressure applied to the pressure measurement units 100a-2 and 100b-2 is correct input that is input from a patient or wrong input by another object (e.g., stuffs in a bag). That is, the biosensors 100a-3 and 100b-3 can prevent pain measurement from being performed due to wrong input by another object except for the human body. The biosensors 100a-3 and 100b-3 may be metal electrostatic sensor, depending on embodiments, and may be disposed at the pressure measurement units 100a-2 and 100b-2.

Next, the trigger buttons 100a-4 and 100b-4 can receive input about a peak pain that is instantaneously generated from a patient.

For example, when the first and second pain-monitoring devices 100a and 100b including the trigger buttons 100a-4 and 100b-4 get peak pain information of a patient through the trigger buttons 100a-4 and 100b-4 while obtaining pain intensity and a pain pattern through the pressure measurement units 100a-2 and 100b-2, the first and second pain-monitoring devices 100a and 100b can detect more accurate pain intensity and pain pattern information by applying a predetermined weight value to the pain intensity and pain pattern.

Next, the touch screens 100a-5 and 100b-5 can get input about at least one of pain body part, pain type, and pain kind information that is user-input pain information from a patient. Further, the touch screens 100a-5 and 100b-5 can also get input about additional abnormal reaction information from a patient.

In detail, the touch screens 100a-5 and 100b-5 can output a body shape and/or name through the display to obtain pain body part information and can obtain pain body part information in accordance with touch input of the patient for the output body shape and/or name.

Further, in an embodiment, the touch screens 100a-5 and 100b-5 can output categories such as somatic pain, visceral pain, and/or neuropathic pain through the display to obtain pain type information, and can obtain pain type information in accordance with touch input of the patient based on the output categories.

Further, the touch screens 100a-5 and 100b-5 can output at least one or more of nociceptive, inflammatory, neuropathic, and functional pain categories through the display to obtain pain kind information, and can obtain pain kind information in accordance with touch input of the patient based on the output categories.

Further, the touch screens 100a-5 and 100b-5 can output categories about symptoms such as a feeling of vomiting, a vertigo, depression, fatigue, pyrexia, and/or convulsions through the display to obtain additional abnormal reaction information, and can obtain additional abnormal reaction information in accordance with touch input of the patient based on the output categories.

In another embodiment, the first and second pain-monitoring devices 100a and 100b may get input of pain body part, pain type, or pain kind information in addition to pain intensity in accordance with a pattern of applying a grip by a user. In detail, the pressure measurement units 100a-2 can sense a grip pattern value for each position to sense a changes of a grip for the position of each of user's fingers. For example, the pressure measurement units 100a-2 can sense grip pattern values for every position for discriminating a grip pattern that is applied mainly by the middle finger and the index finger, a grip pattern that is applied through the ring finger and the middle finger, and a grip pattern that is applied by the ring finger and the little finger. The first and second pain-monitoring devices 100a and 100b can provide an interface that enables a user to simultaneously input a body part and a pain level only with the force of each finger even without input for designating a specific pain body part by matching a pain body part to each grip pattern.

As described above, the first and second pain-monitoring devices 100a and 100b is implemented in a type that enables a patient to easily input a grip using a hand, measures the degree of a pain according to a grip of a patient using the depression sensor, and display and get input of information related to the pain through the display, whereby the first and second pain-monitoring devices 100a and 100b can enable a patient to intuitively input user-input pain information using the pain-monitoring devices when a pain is generated.

Further, the first and second pain-monitoring devices 100a and 100b have a structure that enables easy input of grip input while being held by hand and enables a thumb that is free from grip input can apply touch input through the touch screens 100a-5 and 100b-5, thereby being able to have a structure through which various items of information can be simply input.

In detail, referring to FIG. 3A, the body unit 100a-1 of the first pain-monitoring device 100a has a shape that can be easily held, and the pressure measurement unit 100a-2 that is inserted into the body unit 100a-1 when pressure is applied may be disposed on a side of the body unit 100a-1. That is, a space that can accommodate the pressure measurement unit 100a-2 is provided in the body unit 100a-1, and an elastic member that is supported by the body unit 100a-1 may be disposed in the pressure measurement unit 100a-2. Accordingly, when a user applies pressure while holding the body unit 100a-1 and the pressure measurement unit 100a-2, a grip is transmitted to the elastic member, so pressure due to the grip can be sensed. As the elastic member contracts, the pressure measurement unit 100a-2 is inserted into the body unit 100a-1, and when the grip is removed, the elastic member is elastically deformed and the pressure measurement unit 100a-2 can be discharged back.

The touch screen 100a-5 is disposed on the top of the body unit 100a-1, thereby being able to have a shape that enables touch input through a thumb while being held by hand.

Further, referring to FIG. 4, the body unit 100b-1 of the second pain-monitoring device 100b has a circular structure, and the pressure measurement unit 100b-2 may be disposed on at least a portion of the outer circumferential surface. Accordingly, a user holds a side of the pressure measurement unit 100b-2 with a palm and holds the other side with fingers, so the user can input a grip to the pressure measurement unit 100b-2 by applying pressure through the fingers and the palm. The pressure measurement unit 100b-2 may be made of material having elasticity such as rubber and an elastic member is further disposed in the pressure measurement unit 100b-2, so it is possible to measure pressure due to a grip that is applied from a user through the elastic member.

The touch screen 100b-5 is disposed at the center of the body unit 100b-1, so a user can apply touch input to the touch screen 100b-5 through a thumb while holding the pressure measurement unit 100b-2.

The second pain-monitoring device 100b can also get input of input pain information correction and pain body part information through the touch screen 100b-5. Meanwhile, FIGS. 5A and 5B are examples schematically showing the external appearance of a pain-monitoring device according to another embodiment of the present disclosure.

Referring to FIGS. 5A and 5B, a third pain-monitoring device 100c according to another embodiment of the present disclosure may be implemented to include a plurality of buttons that are shaped such that body parts are intuitionally recognized.

In detail, the third pain-monitoring device 100c may include a body unit 100c-1, a pain part input unit 100c-2, a pain intensity input unit 100c-3, a pain addition information input unit 100c-4, and another input unit 100c-5.

First, the body unit 100c-1 forms the external appearance of the third pain-monitoring device 100c and may be equipped with/include various units for activating the pain-monitoring device inside and outside.

Next, the pain part input unit 100c-2 can get input of what part of the patient body a pain has been generated at, from the patient.

In this case, depending on embodiments, the pain part input unit 100c-2 can get input of a patient about pain body part information by providing a plurality of buttons that are matched to body parts, respectively.

In detail, the pain part input unit 100c-2 may be disposed on a surface of the third pain-monitoring device 100c. For example, the pain part input unit 100c-2 may include a plurality of input buttons showing a plurality of body parts, respectively.

In more detail, referring to FIG. 5A, the pain part input unit 100c-2 may include a first input unit indicating a head, at least one second input unit indicating a body, at least one third input unit indicating a left arm, a least one fourth input unit indicating a right arm, at least one fifth input unit indicating a left leg, and at least one sixth input unit indicating a right leg.

The pain part input unit 100c-2 has a structure enabling a patient to easily input a body part where the patient feels a pain by intuitionally matching the body part to at least one of the plurality of input buttons.

Further, the pain part input unit 100c-2 can enable the pain-monitoring device to detect a pain pattern by obtaining a pressing time for which a patient applies pressure to at least one of the plurality of input buttons.

The plurality of input buttons of the pain part input unit 100c-2 each may include a light emission unit therein. In detail, when a patient presses at least one button for a pain that the patient feels, the light emission unit is turned on, so the patient can accurately recognize where the body part input by the patient is.

That is, a patient can accurately input a body part where the patient feels a pain through the pain part input unit 100c-2.

Next, the pain intensity input unit 100c-3 can get input of the intensity of a pain generated in a patient, that is, strength/weakness information of a pain.

In this case, the pain intensity input unit 100c-3 according to an embodiment may include a plurality of input buttons for inputting pain intensity. For example, when a level range of a pain is defined from 1 to 9, the pain intensity input unit 100c-3 may include level input buttons matched to 1 to 9, respectively. Accordingly, a patient can conveniently input pain intensity by determining the level of a pain through one-time input.

Next, the pain addition information input unit 100c-4 can get input about at least one of pain type, pain kind, and additional abnormal reaction information from a patient.

In this case, depending on embodiments, the pain addition information input unit 100c-4 may be implemented as a touch panel, can get input of a patient for at least one of pain type, pain kind, and additional abnormal reaction information through the touch panel, and can output various items of information about pain information of a patient as a graphic image.

In detail, the pain addition information input unit 100c-4 can output categories such as somatic pain, visceral pain, and/or neuropathic pain through the touch panel, and can obtain pain type information in accordance with touch input of a patient based on the output categories.

Further, the pain addition information input unit 100c-4 can output at least one or more of nociceptive, inflammatory, neuropathic, and functional pain categories through the touch panel, and can obtain pain kind information in accordance with touch input of the patient on the basis of the output categories.

Further, the pain addition information input unit 100c-4 can output categories about symptoms such as a feeling of vomiting, a vertigo, depression, fatigue, pyrexia, and/or convulsions through the touch panel, and can obtain additional abnormal reaction information in accordance with touch input of the patient based on the output categories.

Further, the pain addition information input unit 100c-4 may be disposed on a surface of the third pain-monitoring device 100c. In detail, the pain addition information input unit 100c-4 may be disposed on another surface of one surface of the third pain-monitoring device 100c on which the pain part input unit 100c-2 is disposed.

Meanwhile, the pain part input unit 100c-2, the pain intensity input unit 100c-3, and the pain addition information input unit 100c-4, depending on embodiments, may be implemented in at least any one type of a display (touch panel) type or a button type.

In another embodiment, the pain part input unit 100c-2, the pain intensity input unit 100c-3, and the pain addition information input unit 100c-4 can change a menu, etc. displayed on the display unit 130 when a patient presses an input button short, and can increase or decrease numbers such as paint intensity and pain generation time point information at each predetermined time when a patient presses an input button long.

In detail, in another embodiment, the pain part input unit 100c-2, the pain intensity input unit 100c-3, and the pain addition information input unit 100c-4 may be configured as one input unit to input intensity of a pain in accordance with the time for which an input button matched to a pain body part is pressed.

Further, when a patient stops pressing an input button long, number information related to pain intensity, a pain generation time point, and a pain duration time from the pain generation time point to the time point of stopping pressing the input button may be stored in the storage unit 140.

In another embodiment, the pain part input unit 100c-2, the pain intensity input unit 100c-3, and the pain addition information input unit 100c-4 can get pressure input a plurality of times through an input button, and can measure the intensity of a pain in reverse proportion to the time for which the pressure is applied.

For example, the pain part input unit 100c-2, the pain intensity input unit 100c-3, and the pain addition information input unit 100c-4 can sense a pain when a patient presses an input button a plurality of times with an interval of about 1 seconds as being weaker than a pain when a patient applies pressure with an interval of about 0.5 seconds.

However, the present disclosure is not limited thereto and it may be possible to measure the intensity of pain in proportion to a time difference for applying pressure.

Further, when a patient applies pressure to an input button and does not operate input button for a predetermined time, the pain part input unit 100c-2, the pain intensity input unit 100c-3, and the pain addition information input unit 100c-4 can determine that the time period from the time of first pressure to the time for the last pressure as a time period for which a pain has been generated, that is, a duration time of a pain.

According to this principle, when the input button is implemented as a touch panel, an action by a user of applying pressure to the input button may be an action of touching the display unit 130.

Meanwhile, the other input unit 100c-5 can get input related to various settings such as power on/off, volume adjustment, and/or display type selection input other than the input related to a pain.

As described above, the third pain-monitoring device 100c is implemented such that the type of inputting a body part, information about a pain, etc. can be intuitively recognized, and gets input of user-input pain information from a patient, so it is possible to enable a patient to more quickly and conveniently use the pain-monitoring device when a pain is generated.

Terminal

The terminal 200, in an embodiment of the present disclosure, may include a smartphone, a digital broadcasting terminal, a mobile phone, a PDA (personal digital assistants), a PMP (portable multimedia player), a navigation, a tablet PC, a wearable device, a smart glass, etc. which are mobile terminals in which a program or an application for performing a pain-monitoring service is installed.

The terminal 200 may further include a device in which a program or an application for performing a pain-monitoring service on the basis of wired/wireless communication is installed such as a personal computer including a desktop PC that is a fixed-type terminal, a notebook computer (laptop computer), and an ultrabook.

FIG. 6 is an example showing the terminal 200 according to an embodiment of the present disclosure.

Referring to FIG. 6, the terminal 200 may include a data communication unit 210, a processor 220, etc., and may be classified into a monitoring terminal 200-1 (a patient terminal) and an examination assistant terminal 200-2 (a medical personnel terminal) in an embodiment of the present disclosure.

The monitoring terminal 200-1 may be a terminal 200 that a patient usually uses and the examination assistant terminal 200-2 may be a terminal 200 for a doctor that usually examines patients.

The monitoring terminal 200-1 and the examination assistant terminal 200-2 are provided to classify the use subjects, and the functional characteristics that the terminal 200 performs may be the same.

Meanwhile, in an embodiment of the present disclosure, the pain-monitoring device 200 may directly perform the functions that are performed in the terminal 200.

In an embodiment, the terminal 200 can perform the pain grade calibration described above on the basis of user-input pain information that is received from the pain-monitoring device 100, and the pain-monitoring device 100 may directly perform the pain grade calibration that can be performed in the terminal 200.

Further, in an embodiment of the present disclosure, the pain-monitoring device 100 can directly perform the functional characteristics of the terminal 100 to be described below through the control unit 160.

Hereafter, it is described that the terminal 200 perform the functions to be described below as a subject, but as described above, it would be easily understood by those skilled in the art that the pain-monitoring device 100 can perform the functions to be described below.

In detail, first, the monitoring terminal 200-1 can receive and store user-input pain information input through the pain-monitoring device 100.

Further, the monitoring terminal 200-1 can collect other pain information on the basis of the user-input pain information.

For example, the monitoring terminal 200-1 can collect pain generation time information on the basis of pain generation time point information of the user-input pain information. In another example, the monitoring terminal 200-1 can collect surrounding environmental information (temperature, humidity, weather, and/or location, etc.) on the basis of location information of the pain-monitoring device 100 matched to the user-input pain information. In another example, the monitoring terminal 200-1 can collect pain cycle information on the basis of pain pattern information of the user-input pain information.

As described above, the monitoring terminal 200-1 collecting other pain information can create updated pain information by adding the collected other pain information to the pain information of the corresponding patient.

Further, the monitoring terminal 200-1 generating the updated pain information can output and provide the updated pain information to the patient (user) through a display.

Further, the monitoring terminal 200-1 can transmit the updated pain information to the pain-monitoring server 300 so that the updated pain information is used for the pain-monitoring service.

In an embodiment of the present disclosure, it was described that the terminal 200 receives user-input pain information from the pain-monitoring device 100, collects other pain information, updates pain information, and transmits the updated pain information to the pain-monitoring server 300, but in other various embodiments, the pain-monitoring server 300 and/or the pain-monitoring device 100 may perform the operation described above.

Further, in another embodiment, the monitoring terminal 200-1 may perform the function of the pain-monitoring device 100 by storing an application implementing the pain-monitoring device 100 as a program in a memory, and reading out the application from the memory.

Meanwhile, the examination assistant terminal 200-2 can display a pain data chart provided by the pain-monitoring service as medical council assistant contents.

In this case, the pain data chart, which is a chart generated on the basis of pain information of a patient, may be information obtained by visualizing pain information of a patient through various graphs and/or heat maps.

The heat map is a graph characterized by outputting various items of information that can be shown by colors as a visual graph having rows on a predetermined image. In an embodiment, the heat map may be a graph showing the factors (e.g., paint intensity) of pain information using colors and/or symbols on a graph in which the horizontal axis is set as date and the vertical axis is set as time.

That is, the pain data chart visualizes and provides pain information of a patient such that the pain-related condition of the patient is easily and intuitively recognized and analyzed.

Further, the medical council assistant contents are data that are formed by combining medical images, videos, animations, of texts and displayed through the terminal 200 to assist medical councils.

In detail, the medical council assistant contents may include audio-visual data for assisting medical councils. In detail, the audio-visual data may include pain management contents, diabetes management contents, disease diagnosis contents, treatment method contents, medicine council contents, examination cost contents, insurance information contents, sign content, other contents, and medical council contents combining these contents.

For example, in the medical council assist contents, at least one image or items of information of patient pain information, body organ images, disease information, treatment method images, treatment method information, medicine-taking method, medicine information, and insurance information may be included, and audio information that is used to construct the medial council information may also be additionally included.

Further, in an embodiment, the medical council assistant contents may be visual contents generated on the basis of at least one or more medical data (Electric Health Record (EHR)).

Further, the medical council assistant contents may include an electronic medical record (EMR) received from a hospital server or hospital database.

Such various medical council assistant contents are displayed on the examination assistant terminal 200-2 to be used for councils in accordance with selection of a doctor, and the examination assistant terminal 200-2 can arrange and provide a plurality of selected medical council assistant contents for a doctor to easily use them.

Further, the medical council assistant contents provide various types of council input interfaces such that medical council contents matched to medical council subjects and medical council assistant contents are created.

In detail, the medical council contents are contents created by adding council subject matters input by a user (a medical personnel) to the medical council assistant contents described above. That is, the medical council contents may include medical council assistant contents and council subject matters.

In order to create the medical council contents, the examination assistant terminal 200-2 provides a medical council contents construction image composed of medical council assistant contents together with a council input interface, and council subject matters are input to the medical council assistant contents on the basis of the council input interface, whereby medical council contents may be created.

The council input interface may include a graphic user interface that enables a councilor input writing, voice, editing, or images to the displayed medical council assistant image.

For example, the council input interface may provide a writing input interface that senses writing input of a user on the medial council assistant image.

Further, the examination assistant terminal 200-2 can provide the council input interface using a touch screen (touch panel) to receive user input while displaying the medical council assistant image.

Further, the council input interface can provide a voice input interface for inputting council subject matters by matching a recorded council voice to the medical council assistant contents by recording the voice of a user.

That is, the examination assistant terminal 200-2 can display a pain data chart as medical council assistant contents, and can provide medical council contents through the council input interface on the displayed medical council assistant contents.

In this case, the medical council assistant contents and the medical council content displaying the pain data chart may be directly created on the basis of the pain information of a user obtained by the terminal 200, or may be obtained in cooperation with an external server.

Meanwhile, in another embodiment, as described above, the pain-monitoring device 100 may output the pain data chart that is output from the examination assistant terminal 200-2, that is, various embodiments may also be possible.

Pain-Monitoring Server

Meanwhile, the pain-monitoring server 300 in an embodiment of the present disclosure can perform a series of operations for providing a pain-monitoring service in cooperation with the pain-monitoring device 100 and/or the terminal 200.

In detail, first, the pain-monitoring server 300 can receive pain information from the monitoring terminal 200-1, and can store the received pain information in a database for each patient.

Further, the pain-monitoring server 300 can receive and obtain additional bioinformation (sleep and stress index information, etc.) from a device other than a pain-monitoring system.

Further, the pain-monitoring server 300 can update the pain information by adding the obtained additional bioinformation to the pain information of a patient received from the monitoring terminal 200-1.

Further, the pain-monitoring server 300 can create a pain data chart on the basis of the updated pain information.

In detail, referring to FIG. 8, the pain-monitoring server 300 can create a pain data chart that is information obtained by visualizing the pain information of a patient using various graphs and/or heat maps.

In more detail, the pain-monitoring server 300 can create a pain data chart by including at least one or more of a main pain graph, a pain body map, a first relevant graph, a second relevant graph, and a third relevant graph.

More detailed description will be provided below in the pain-monitoring method using the pain-monitoring device 100.

It was described above that the pain-monitoring server 300 performs a series of operations of receiving and storing pain information for each patient, obtaining additional bioinformation, and creating a pain data chart, but in other various embodiments, the terminal 200 and/or the pain-monitoring device 100 may perform the operations.

In detail, in another embodiment, the pain-monitoring device 100 can directly perform the operations through the control unit 160.

In detail, the pain-monitoring device 100 can receive pain information from the monitoring terminal 100-1, and can store the received pain information in a database for each patient.

Further, the pain-monitoring device 100 can create a pain data chart on the basis of the received pain information.

Further, the pain-monitoring device 100 can receive and obtain additional bioinformation (sleep information, stress index information, and/or environmental information (temperature, humidity, weather, and/or location information, etc.)) from a device other than a pain-monitoring system.

The additional bioinformation can be measured and obtained by the pain-monitoring device itself when the device includes a unit that measures exercise information, sleep information, and GPS information.

Further, the pain-monitoring device 100 can update the pain information by adding the obtained additional bioinformation to the pain information of a patient received from the monitoring terminal 200-1.

Further, the pain-monitoring device 100 can create a pain data chart on the basis of the updated pain information.

In detail, referring to FIG. 8, the pain-monitoring device 100 can create a pain data chart that is information obtained by visualizing the pain information of a patient using various graphs and/or heat maps.

Meanwhile, FIG. 7 is a block diagram of the inside of the pain-monitoring server 300 according to an embodiment of the present disclosure.

Referring to FIG. 7, the pain-monitoring server 300 may include a data transceiver 310, a data processor 320, and a database 330.

First, the data transceiver 310 can provide transmit and receive various data for providing the pain-monitoring service to the pain-monitoring device 100, the terminal 200, an external device, and/or an external server through a network.

Next, the data processor can perform a series of data processing for providing the pain-monitoring service.

The data processor 320 can be realized using at least one of application specific integrated circuits (ASICs), digital signal processors (DSPs), digital signal processing devices (DSPDs), programmable logic devices (PLDs), field programmable gate arrays (FPGAs), controllers, micro-controllers, microprocessors, and electronic units for executing other functions.

Finally, the database 330 can store various data related to the pain-monitoring service.

The database 330 may be various storage devices such as a ROM, a RAM, an EPROM, a flash drive, a hard drive, and may be a web storage that performs the storage function of the database 330 on the internet.

Pain-Monitoring Method Using Pain-Monitoring Device

Hereafter, a pain-monitoring method using the pain-monitoring device 100 is described in detail with reference to the accompanying drawings.

FIG. 9 is a flowchart illustrating a pain-monitoring method using the pain-monitoring device 100 according to an embodiment of the present disclosure.

Referring to FIG. 9, first, the pain-monitoring device 100 can obtain user-input pain information of a patient (S101).

In detail, the pain-monitoring device 100 can obtain user-input pain information including at least one or more of items of information of pain body part, pain intensity (i.e., pain grade), pain pattern, pain type, pain kind, and additional abnormal reaction information of a patient through the input unit 110.

In this case, the pain-monitoring device 100 can determine paint intensity (a pain grade) that the patient wants to input on the basis of pressure input obtained from the patient.

In this case, the pain-monitoring device 100 can perform pain grad calibration that standardizes a pain grade into an individual customized type on the basis of a grip obtained from the patient to obtain accurate pain intensity considering individual differences of patients.

In detail, the pain-monitoring device 100 may perform pain grade calibration when the pain-monitoring device 100 is initially reset, when user change or re-registration is performed on an application related pain-monitoring of the terminal 200 that operates with the pain-monitoring device 100, or when the configuration of the pain-monitoring device 100 is reset and/or the configuration of the application is reset.

In more detail, the pain-monitoring device 100 can measure the maximum pressure value at least twice or more when a patient strongly holds the input unit to perform the pain grade calibration.

Further, the pain-monitoring device 100 can set a predetermined pressure value corresponding to the maximum pain grade by matching the measured maximum pressure value to the maximum pain grade showing the maximum degree of pain of a plurality of pain grades.

Further, the pain-monitoring device 100 can set predetermined pressure values matched to the other lower pain grades except for the maximum pain grade on the basis of the measured maximum pressure value. In detail, the pain-monitoring device 100 can set pressure values matched to the other lower pain grades by performing reverse operation for the lower pain grades on the basis of the maximum pressure value.

For example, when the pain grades are composed of grades 1 to 10 and the maximum pressure value is matched to the grade 10 that is the maximum pain grade, the pain-monitoring device 100 can perform sequential reverse operation from the grade 10 to the other lower pain grades 9 to 1 on the basis of the maximum pressure value that is the pressure value for the grade 10. Further, the pain-monitoring device 100 can set a pressure value for each pain grade by matching the input value obtained through reverse operation for each grade to each grade Meanwhile, in more detail, in accordance with an embodiment, the first and second pain-monitoring devices 100a and 100b can obtain pain intensity (pain grade) and/or pain pattern information that are user-input pain information on the basis of the degree of pressure (a grip) and/or a pressing time obtained by pressure (grip) input of a patient.

Further, the first and second pain-monitoring devices 100a and 100b can obtain at least one or more items of information of pain body part, pain type, pain kind, and additional abnormal reaction information in accordance with touch input of a patient through the touch screens 100a-5 and 100b-5.

Meanwhile, in accordance with an embodiment, the third pain-monitoring device 100c can obtain information about at least one or more of pain intensity, pain pattern, pain body part, pain kind, pain type, and additional abnormal reaction information on the basis of input of a user for the pain part input unit 100c-2, the pain intensity input unit 100c-3, and the pain addition information input unit 100c-4 that are implemented by at least one of a display (touch panel) type or a button type.

As described above, the pain-monitoring device 100 obtain the user-input pain information in accordance with input of a patient can transmit the obtained user-input pain information to the monitoring terminal 200-1.

The monitoring terminal 200-1 receiving the user-input pain information from the pain-monitoring device 100 can store the received user-input pain information in a memory (S103).

Further, the monitoring terminal 200-1 can collect other pain information on the basis of the received user-input pain information and can update the pain information by adding the collected other pain information to the pain information of the patient (S105).

That is, the monitoring terminal 200-1 can create updated pain information by adding the collected other pain information to the pain information of the patient.

In detail, the monitoring terminal 200-1 can obtain other pin information including pain generation time information, surrounding environment information, a pain cycle, etc. on the basis of the received user-input pain information.

In more detail, the monitoring terminal 200-1 can obtain pain generation time information on the basis of pain generation time point information of the user-input pain information.

Further, in an embodiment, the monitoring terminal 200-1 can collect surrounding environmental information (temperature, humidity, weather, and/or location, etc.) on the basis of location information of the pain-monitoring device 100 matched to the user-input pain information.

Further, in an embodiment, the monitoring terminal 200-1 can collect pain cycle information on the basis of pain pattern information of the user-input pain information.

Further, the monitoring terminal 200-1 collecting other pain information can create updated patient pain information by adding the collected other pain information to the pain information of the corresponding patient.

As described above, the monitoring terminal 200-1 can include and user even pain information that a patient has difficulty in inputting one by one in the pain information by automatically collecting additional information (e.g., pain generation time information, surrounding environment information, etc.) related to a corresponding pain on the basis of the pain information input by the patient, and can improve objectivity of patient examination by giving assistance to be able to analyze the pain state of a patient on the basis of much information.

Next, the monitoring terminal 200-1 updating the pain information by adding other pain information to the pain information can transmit the updated pain information to the pain-monitoring server 300.

Further, the pain-monitoring server 300 receiving the updated pain information can store the received pain information in a database 300 for each patient (S105).

Further, the pain-monitoring server 300 can collect additional bioinformation from a device other than the pain-monitoring system and can update the corresponding pain information by adding the collected bioinformation to the pain information of the patient (S107).

For example, the pain-monitoring server 300 can collect sleep information and/or stress index information of the patient obtained from an external device other than the device included in the pain-monitoring system. Further, the pain-monitoring server 300 can update the pain information by adding the collected sleep information and/or stress index information to the pain information of the corresponding patient.

As described above, there is an effect that the pain-monitoring server 300 can use a large amount of data, from which it is possible to find out what external factors of other than the pain-related information have influenced the pain of the patient, for pain examination by collecting and using additional bioinformation for the pain information.

Next, the pain-monitoring server 300 updating the pain information can create a pain data chart on the basis of the updated pain information (S109).

In detail, referring to FIG. 8, the pain-monitoring server 300 can create a pain data chart, which is obtained by visualizing the pain information of the patient using various graphs and/or heat maps, by including at least one or more of a main pain graph, a pain body map, a first relevant graph, a second relevant graph, and a third relevant graph.

In more detail, the pain-monitoring server 300 can show a main pain graph as a heat map type graph that shows the pain time, date, and/or intensity such that they can be recognized at a glance.

For example, the main pain graph may be implemented in a heat map type in which the horizontal axis is a pain date, the vertical axis is pain time, and marks of pints or circular bars shown in the graphs determine pain intensity, pain duration time, and/or pain date.

In this case, the main pain graph may show the pain intensity by disposing a color mapping guide for each pain degree at a side of the heat map.

Further, the pain-monitoring server 300 can show pain generation part distribution that shows what part of the patient body a pain is generated at through a pain body map.

In this case, when a specific part is designated in the pain body map, the pain-monitoring server 300 can display only the pain value of the corresponding part in the heat map in cooperation with the main pain graph.

That is, the pain body map may be displayed on the pain data chart together with the main pain graph such that where, when, and how much a pain has been generated can be conveniently recognized.

Further, the pain-monitoring server 300 can create and show a specific first relevant graph by extracting and analyzing main data (e.g., pain time, date, and/or intensity, etc.) of the pain information.

In an embodiment, the first relevant graph may include a maximum-pain variation transition graph and/or a continuous pain change graph that is created by analyzing the main data of the pain information.

In detail, the pain-monitoring server 300 can show the maximum-pain variation transition graph, which shows an everyday maximum pain value that can show whether the paint of a patient is a temporal acute pain or is being developed into a long-period chronic pain, in the pain data chart by analyzing the main date of the pain information.

Further, the pain-monitoring server 300 can show a continuous pain change graph, which can show how the transition of a continuous pain from yester to that day of the patient is, in a point graph type in the pain data chart by analyzing the main data of the pain information.

As described above, the pain-monitoring server 300 can enable the pain state of a patient to be recognized in detail by providing a graph created by deeply analyzing the main data of obtained pain information.

Further, the pain-monitoring server 300 can create and show a second relevant graph on the basis of the additional bioinformation obtained from a device other than the pain-monitoring system.

In detail, the pain-monitoring server 300 can create and show a sleep graph and/or a stress graph in the pain data chart on the basis of additional bioinformation such as sleep information and/or stress index information of a patient obtained form an external device.

Further, the pain-monitoring server 300 can create and show a third relevant graph on the basis of other pain information of the pain information.

In detail, the pain-monitoring server 300 can create and show a pain frequency graph based on weather and a pain part graph based on time on the basis of other pain information including at least one or more of pain generation visual information and patient-surrounding environment information (temperature, humidity, weather, and/or location, etc.) additionally collected on the basis of user-input pain information.

In detail, the pain frequency graph based on weather makes it possible to find out the correlation of several factors related to how corresponding weather influences a pain on the basis of pain generation frequency statistics according to weather such as 'rain/humidity, the amount of wind, low temperature, a large daily temperature range', etc.

Further, the pain part graph based on time makes it possible to find out what time a pain gets severe at for each body part.

As described above, there is an effect that the pain-monitoring server 300 provides the second relevant graph and/or the third relevant graph based on additional bioinformation and/or other pain information, thereby being able to make it possible to recognize the patient state on the basis of main factors related to the pain of the patient and external factors and to perform pain examination in various respects, to generally analyze the pain state of the patient using information in a wider range, and to improve objectivity of patient examination.

Further, the pain-monitoring server 300 provides a pain data chart that is information visualized using pain information including various items of pain-related information, as described above, thereby being able to make it possible to generally analyze a plurality of pain-related data and to more intuitionally and conveniently check the pain state of the patient.

Next, the pain-monitoring server 300 creating the pain data chart can transmit the created pain data chart to the examination assistant terminal 200-2 or the monitoring terminal 200-1.

Further, the examination assistant terminal 200-2 or the monitoring terminal 200-1 receiving the pain data chart can provide the received pain data chart as a graphic image (S111, S113).

In particular, the examination assistant terminal 200-2 can output the received pain data chart as medical council assistant contents.

In detail, the examination assistant terminal 200-2 can provide the pain data chart as medical council assistant content through a medical council assistant program, which is operated in cooperation with an application installed in the terminal 200 and/or an external server.

Further, the examination assistant terminal 200-2 can provide medical council contents created on the basis of input by a medical personnel using a council input interface by providing the council input interface through the medical council assistant contents showing the pain data chart.

As described above, the examination assistant terminal 200-2 can improve usability of pain-related data visualized through various interfaces by providing a pain data chart through medical council assistant contents and/or medical council contents, can contributes effective understanding by intuitionally recognizing the pain state of a patient, and can improve the quality of examination through pain monitoring.

There is an effect that the pain-monitoring device and method according to an embodiment of the present disclosure monitors a pain of a patient that is generated in various situations, creates quantified data on the basis of the pain that the patient feels and information related to the pain, and provides an individual customized diagnosis/examination service for the corresponding pain on the basis of the data, thereby being able to achieve patient-customized diagnosis based on information obtained by quantifying/patterning the relationship between the pain of the patient and various factors related to the pain of the patient.

Further, there is an effect that the pain-monitoring device and method according to an embodiment of the present disclosure can more accurately sense the degree of a pain that a patient wants to input by standardizing the grade of a patient sensed on the basis of a grip in consideration of individual differences of grips obtained from patients.

Further, there is an effect that the pain-monitoring device and method according to an embodiment of the present disclosure can device a diagnosis result on the basis of more objective and accurate information when examining a patient by creating and providing information visualized on the basis of pain-related information of the patient obtained through continuous monitoring, thereby being able to improve the quality of patient examination and derive appropriate following measures.

Further, there is an effect that the pain-monitoring device and method according to an embodiment of the present disclosure can generally analyze and check a plurality of pain-related data by creating and providing information visualized using pain information including various items of pain-related information.

Further, there is an effect that the pain-monitoring device and method according to an embodiment of the present disclosure can overcome the problem of a diagnosis error and deterioration of objectivity that are generated when various items of pain-related information depends on only the memory of a patient by automatically obtaining pain-related data of a patient through a series of operations that are implemented in a pain-monitoring system.

Further, there is an effect that the pain-monitoring device and method according to an embodiment of the present disclosure can use even pain-related information that a patient has difficulty in inputting one by one by automatically collecting additional information related to a corresponding pain on the basis of pain information input by a patient.

Further, there is an effect that the pain-monitoring device and method according to an embodiment of the present disclosure can assist analysis of the pain state of a patient on the basis of a wider information and can improve objectivity of the analysis by providing visualized information for pain monitoring by using even pain-related information automatically collected, in addition to the pain information input by the patient.

Further, there is an effect that the pain-monitoring device and method according to an embodiment of the present disclosure can use a large amount of data, which makes it possible to find out what external factors have influenced a pain other than pain-related information, for pain examination by collecting additional bioinformation related to a patient from a device other than the pain-monitoring system.

Further, there is an effect that the pain-monitoring device and method according to an embodiment of the present disclosure makes it possible to more intuitionally and conveniently check the pain state of a patient by creating and providing visualized data using various graphs and charts on the basis of pain information of the patient.

Further, there is an effect that the pain-monitoring device and method according to an embodiment of the present disclosure can improve usability of visualized pain-related data through various interfaces by providing pain information of a patient through medical council assistant contents and/or medical council contents, can contributes effective understanding by intuitionally recognizing the pain state of a patient, and can improve the quality of examination through pain monitoring.

Further, there is an effect that the pain-monitoring device and method according to an embodiment of the present disclosure can improve the quality of general life of a patient in addition to disease management of the patient by monitoring and managing changes of a pain and changes of symptoms of the patient, can efficiently adjust use of medicines that is applied to the patient, can find out early and prevent complications that may generated in the patient, and correspondingly can reduce social-medical costs.

Further, there is an effect that the pain-monitoring device and method according to an embodiment of the present disclosure can contribute achieve industrialization based on development and copyrighting of an algorithm through construction of big data by monitoring and managing changes of a pain and changes of symptoms of a patient using quantified data.

Embodiments of the present disclosure described above may be implemented in the type of program commands the can be executed through various computer components, and may be recorded on a computer-readable recording medium. The computer-readable recording medium may include program commands, data files, and data structures individually or in combinations thereof. The program commands that are recorded on a computer-readable recording medium may be those specifically designed and configured for the present invention or may be those available and known to those engaged in computer software in the art. The computer-readable recording medium includes magnetic media such as hard disks, floppy disks, and magnetic media such as a magnetic tape, optical media such as CD-ROMs and DVDs, magneto-optical media such as floptical disks, and hardware devices specifically configured to store and execute program commands, such as ROM, RAM, and flash memory. The program commands include not only machine language codes compiled by a compiler, but also high-level language code that can be executed by a computer using an interpreter etc. A hardware device may be changed into one or more software module to perform the processes according to the present disclosure, and vice versa.

Specific execution described herein is embodiments and does not limit the present disclosure in any way. For briefness of the specification, electronic components, control systems, and software of the related art, and other functions of the system may not be described. Furthermore, wire connection and connecting members of components shown in the figures are examples of functional connection and/or physical or circuit connections, and in actual devices, they may be replaceable or may be shown as various additional functional connection, physical connection, or circuit connection. Unless stated in detail such as "necessary" and "important", they may not be necessary component for the present disclosure.

Although exemplary embodiments of the present disclosure were described above, it should be understood that the present disclosure may be changed and modified in various ways by those skilled in the art without departing from the spirit and scope of the present disclosure described in the following claims. Therefore, the technical scope of the present disclosure is not limited to the exemplary embodiments described herein, but should be determined by claims.

The present disclosure relates to a pain-monitoring device for monitoring a pain of a patient, so it has industrial applicability. Further, the present disclosure relates to a pain-monitoring method of monitoring a pain on the basis of data input from the pain-monitoring device, so it has industrial applicability.

What is claimed is:

1. A pain-monitoring method in which a processor of an examination assistant terminal using user-input pain information obtained by a pain-monitoring device provides a pain monitoring service, the method comprising:
   the pain monitoring device comprising:
   an input unit for sensing pain-related input of a user;
   a display unit for outputting pain-related information; and
   a control unit for controlling the input unit and the display unit,
   wherein the input unit includes a touch input unit sensing touch input of the user, a pressure measurement unit measuring pressure input of the user and a trigger button receiving input from the user for a temporal pain,
   the pain-monitoring method comprising:
   obtaining user-input pain information including pain intensity from the pain-monitoring device;
   transmitting and storing the obtained user-input pain information to a monitoring terminal;
   updating the stored user-input pain information by adding other pain information collected by the monitoring terminal;
   transmitting and storing the updated user-pain information to a pain-monitoring server;
   creating a pain data chart on the basis of the updated user-pain information and bioinformation of the user collected by the pain-monitoring server; and
   displaying the created pain data chart through the monitoring terminal and the pain-monitoring server,
   wherein the obtaining user-input pain information including pain intensity from the pain-monitoring device includes,
   creating the user-input pain information in accordance with the sensed pressure input and touch input by the control unit; and
   creating the user-input pain information when input through the trigger button is sensed.

2. The pain-monitoring method of claim 1, wherein the creating of a pain data chart on the basis of the pain information includes creating at least one or more of a main pain graph, a pain body map, a first relevant graph, a second relevant graph, and a third relevant graph on the basis of the pain information.

3. The pain-monitoring method of claim 2, wherein the main pain graph is a graph showing the user-input pain information accumulated for a plurality of days as a heat map.

4. The pain-monitoring method of claim 1, wherein the other pain information includes pain generation time information, surrounding environment information and a pain cycle.

5. The pain-monitoring method of claim 1, wherein the bioinformation of the user collected by the pain-monitoring server includes sleep information and/or stress index information of the user.

* * * * *